(12) United States Patent
Co

(10) Patent No.: US 6,210,671 B1
(45) Date of Patent: Apr. 3, 2001

(54) HUMANIZED ANTIBODIES REACTIVE WITH L-SELECTIN

(75) Inventor: Man Sung Co, Cupertino, CA (US)

(73) Assignee: Protein Design Labs, Inc., Fremont, CA (US)

(*) Notice: Subject to any disclaimer, the term of this patent is extended or adjusted under 35 U.S.C. 154(b) by 0 days.

(21) Appl. No.: 08/579,378

(22) Filed: Dec. 27, 1995

Related U.S. Application Data

(63) Continuation-in-part of application No. 08/160,074, filed on Nov. 30, 1993, now abandoned, which is a continuation-in-part of application No. 07/983,946, filed on Dec. 1, 1992, now abandoned.

(30) Foreign Application Priority Data

Aug. 17, 1995 (EP) ................................. 95 112 895
Sep. 19, 1995 (EP) ................................. 95 114 696

(51) Int. Cl.[7] ................................. A61K 39/395
(52) U.S. Cl. ................................. 424/154.1; 424/130.1; 424/133.1; 424/141.1; 424/143.1; 424/144.1; 424/153.1; 424/173.1; 435/326; 435/328; 435/332; 435/343; 435/343.1; 435/343.2; 530/387.1; 530/387.3; 530/388.1; 530/388.2; 530/388.22; 530/388.7; 530/388.73; 530/388.75; 536/23.1; 536/23.5; 536/23.53
(58) Field of Search ................................. 424/130.1, 132.1, 424/133.1, 141.1, 143.1, 144.1, 153.1, 154.1, 173.1; 435/69.6, 172.3, 252.3, 320.1, 70.21, 452, 326, 328, 332, 334, 343, 343.1, 343.2, 346; 536/23.4, 23.5, 23.53; 530/387.1, 387.3, 388.1, 388.22, 388.7, 388.73, 388.75, 388.2

(56) References Cited

U.S. PATENT DOCUMENTS

| 5,316,913 | * | 5/1994 | Butcher et al. | 435/7.24 |
| 5,530,101 | * | 6/1996 | Queen et al. | 530/387.3 |
| 5,679,346 | * | 10/1997 | Tedder et al. | |

FOREIGN PATENT DOCUMENTS

0440351 * 1/1991 (EP) .

OTHER PUBLICATIONS

Edgington Biotechnology 10: 383–389 (1992).*
Ward et al. Therapeutic Immunology : 1: 165–171 (1994).*
Waldmann Science 252: 1657–1662 (1981).*
Kishimoto Blood 78: 805–811 (1991).*
Kishimoto PNAS 87: 2244–2248 (1990).*
Von Anorian et al. PNAS 88: 7538–7542 (1991).*
Carlos Immunol. Rev. 114: 5–28 (1990).*
Kahan Cur. Opin Immunol. 4: 553–560 (1992).*
Albelda et al. FASEB Journal 8: 504–512 (1994).*
Welply et al. Biochimia et Biophysica Acta 1197: 215–226 (1994).*
Paul (Ed) Fundamental Immunology Raven Press 1993 p. 242 only.*

* cited by examiner

*Primary Examiner*—Phillip Gambel
(74) *Attorney, Agent, or Firm*—Townsend & Townsend & Crew

(57) ABSTRACT

Humanized immunoglobulins specifically reactive with L-selectin are prepared employing recombinant DNA technology for use in e.g., treatment of inflammatory disorders.

17 Claims, 13 Drawing Sheets

```
                         .               .         30                .               .         60
ATGGAATCACAGACCCAGGTCCTCATGTTTCTTCTGCTCTGGGTATCTGGTGCCTGTGCA
 M   E   S   Q   T   Q   V   L   M   F   L   L   L   W   V   S   G   A   C   A

.               .         90                .               .        120
GACATTGTGATGACACAGTCTCCATCCTCCCTGGCTATGTCAGTAGGACAGAAGGTCACT
 D   I   V   M   T   Q   S   P   S   S   L   A   M   S   V   G   Q   K   V   T

.               .        150                .               .        180
ATGACCTGCAAGTCCAGTCAGAGCCTTTTAAATAGTAGCAATCAAAAGAACTATTTGGCC
 M   T   C   K   S   S   Q   S   L   L   N   S   S   N   Q   K   N   Y   L   A

.               .        210                .               .        240
TGGTACCAGCAGAAACCAGGACAGTCTCCTAAACTTCTGGTATACTTTGCATCCACTAGG
 W   Y   Q   Q   K   P   G   Q   S   P   K   L   L   V   Y   F   A   S   T   R

.               .        270                .               .        300
GAATCTGGGGTCCCTGATCGCTTCATAGGCAGTGGATCTGGGACAGATTTCACTCTTACC
 E   S   G   V   P   D   R   F   I   G   S   G   S   G   T   D   F   T   L   T

.               .        330                .               .        360
ATCAGCAGTGTGCAGGCTGAAGACCTGGCAGATTACTTCTGTCACCAACATTATAGCACT
 I   S   S   V   Q   A   E   D   L   A   D   Y   F   C   H   Q   H   Y   S   T

.               .        390
CCGCTCACGTTCGGTGCTGGGACCAAGCTGGAGCTGAAA
 P   L   T   F   G   A   G   T   K   L   E   L   K

FIG. 1A

.               .         30                .               .         60
ATGGAATGGAGTTGGATATTTCTCTTTCTCCTGTCAGGAACTGCAGGTGTCCACTCTGAG
 M   E   W   S   W   I   F   L   F   L   L   S   G   T   A   G   V   H   S   E

.               .         90                .               .        120
GTCCAGCTGCAGCAGTCTGGACCTGACCTGGTAAAGCCTGGGGCTTCAGTGAAGATGTCC
 V   Q   L   Q   Q   S   G   P   D   L   V   K   P   G   A   S   V   K   M   S

.               .        150                .               .        180
TGCAAGGCTTCTGGATACACATTCACTAGCTATGTTATGCACTGGGTGAAGCAGAAGCCT
 C   K   A   S   G   Y   T   F   T   S   Y   V   M   H   W   V   K   Q   K   P

.               .        210                .               .        240
GGGCAGGGCCTTGAGTGGATTGGATATATTTATCCTTACAATGATGGTACTAAGTACAAT
 G   Q   G   L   E   W   I   G   Y   I   Y   P   Y   N   D   G   T   K   Y   N

.               .        270                .               .        300
GAGAAGTTCAAAGGCAAGGCCACACTGACTTCAGACAAATCCTCCAGCACAGCCTACATG
 E   K   F   K   G   K   A   T   L   T   S   D   K   S   S   S   T   A   Y   M

.               .        330                .               .        360
GAGCTCAGCAGCTTGACCTCTGAGGACTCTGCGGTCTATTACTGTGCAAGGGAGGAGTAT
 E   L   S   S   L   T   S   E   D   S   A   V   Y   Y   C   A   R   E   E   Y

.               .        390                .               .        420
GGTAACTACGTTCGGTACTTCGATGTCTGGGGCGCAGGGACCACGGTCACCGTCTCCTCA
 G   N   Y   V   R   Y   F   D   V   W   G   A   G   T   T   V   T   V   S   S

```
         10        20        30        40        50        60
TCTAGACCACCATGGTTTTCACACCTCAGATACTTGGACTTATGCTTTTTTGGATTTCAG
             M  V  F  T  P  Q  I  L  G  L  M  L  F  W  I  S 70        80        90       100       110       120
CCTCCAGAGGTGACATTCAGATGACACAGTCTCCATCCACTCTGAGTGCATCAGTAGGAG
 A  S  R  G  D  I  Q  M  T  Q  S  P  S  T  L  S  A  S  V  G 130       140       150       160       170       180
ATCGTGTCACTATTACATGTAAGAGCTCACAGAGCCTTTTAAATAGTAGCAATCAAAAGA
 D  R  V  T  I  T  C  K  S  S  Q  S  L  L  N  S  S  N  Q  K 190       200       210       220       230       240
ACTATTTGGCCTGGTACCAGCAGAAACCAGGAAAGGCACCTAAGCTTCTGGTATACTTTG
 N  Y  L  A  W  Y  Q  Q  K  P  G  K  A  P  K  L  L  V  Y  F 250       260       270       280       290       300
CATCCACTAGGGAATCTGGAGTCCCTGATCGCTTCATAGGTAGTGGATCTGGTACAGATT
 A  S  T  R  E  S  G  V  P  D  R  F  I  G  S  G  S  G  T  D 310       320       330       340       350       360
TCACTCTTACCATCAGCAGTCTGCAGCCAGAAGACTTTGCAACATACTTCTGTCACCAAC
 F  T  L  T  I  S  S  L  Q  P  E  D  F  A  T  Y  F  C  H  Q 370       380       390       400       410       420
ATTATAGCACTCCGCTCACGTTCGGTCAAGGTACTAAGGTAGAAGTCAAGCGTAAGTACA
 H  Y  S  T  P  L  T  F  G  Q  G  T  K  V  E  V  K

430
CTTTTCTAGA
```

FIG. 3A

```
         10        20        30        40        50        60
TCTAGACCACCATGGGATGGAGCTGTATCATCCTCTTCTTGGTAGCAACAGCTACAGGTG
             M  G  W  S  C  I  I  L  F  L  V  A  T  A  T  G 70        80        90       100       110       120
TCCACTCCCAGGTCCAGCTGGTACAGTCTGGAGCTGAAGTCAAGAAACCTGGGAGCTCAG
 V  H  S  Q  V  Q  L  V  Q  S  G  A  E  V  K  K  P  G  S  S 130       140       150       160       170       180
TGAAGGTATCCTGCAAGGCTTCTGGATACACATTCACTAGCTATGTTATGCACTGGGTGA
 V  K  V  S  C  K  A  S  G  Y  T  F  T  S  Y  V  M  H  W  V 190       200       210       220       230       240
GACAGGCACCTGGTCAAGGACTCGAGTGGATTGGATATATTTATCCTTACAATGATGGTA
 R  Q  A  P  G  Q  G  L  E  W  I  G  Y  I  Y  P  Y  N  D  G 250       260       270       280       290       300
CCAAGTACAATGAGAAGTTCAAAGGCCGAGTCACAATTACTTCAGACGAGTCCACTAACA
 T  K  Y  N  E  K  F  K  G  R  V  T  I  T  S  D  E  S  T  N 310       320       330       340       350       360
CAGCCTACATGGAACTCAGCAGCTTGCGATCGGAGGACACTGCAGTCTATTACTGTGCAA
 T  A  Y  M  E  L  S  S  L  R  S  E  D  T  A  V  Y  Y  C  A 370       380       390       400       410       420
GGGAGGAGTATGGTAACTACGTTCGGTACTTCGATGTCTGGGGCCAAGGTACACTGGTCA
 R  E  E  Y  G  N  Y  V  R  Y  F  D  V  W  G  Q  G  T  L  V 430       440       450
CAGTCTCCTCAGGTGAGTCCTAACTTCTAGA
 T  V  S  S
```

FIG 3B

```
ATG GAG ACA GAC ACA ATC CTG CTA TGG GTG CTG CTG CTC TGG GTT CCA GGC TCC ACT GGT      60
 M   E   T   D   T   I   L   L   W   V   L   L   L   W   V   P   G   S   T   G

GAC ATT GTG TTG ACC CAA TCT CCA GCT TCT TTG TCT GTG TCT CTA GGG GAG AGG GCC TCC     120
 D   I   V   L   T   Q   S   P   A   S   L   S   V   S   L   G   E   R   A   S

ATC TCC TGC AAG GCC AGC CAA AGT GTT GAT TAT GAT GGT GAT AGT TAT ATG AAC TGG TAC     180
 I   S   C   K   A   S   Q   S   V   D   Y   D   G   D   S   Y   M   N   W   Y

CAA CAG AAA CCA GGA CAG CCA CCC AAA CTC CTC ATC TAT GCT GCA TCC AAT CTA GAA TCT     240
 Q   Q   K   P   G   Q   P   P   K   L   L   I   Y   A   A   S   N   L   E   S

GGG ATC CCA GCC AGG TTT AGT GGC AGT GGG TCT GGG ACA GAC TTC ACC CTC ACC ATC CAT     300
 G   I   P   A   R   F   S   G   S   G   S   G   T   D   F   T   L   T   I   H

CCT GTG GAG GAG GAT GCT GCA ACC TAT TAC TGT CAG CAA AGT AAT GAG GAT CCG TGG         360
 P   V   E   E   D   A   A   T   Y   Y   C   Q   Q   S   N   E   D   P   W

ACG TTC GGT GGA GGC ACC AAG CTG GAA ATC AAA                                         390
 T   F   G   G   G   T   K   L   E   I   K
```

```
ATG AAC TTC GGG TCC AGC TTG ATT TTC                           30                      60
 M   N   F   G   S   S   L   I   F   CTT GTC CTT GTT TTA AAA GGT GTC CAG TGT GAA
                                      L   V   L   V   L   K   G   V   Q   C   E 90                     120
GTG AAA CTG GTG GAG TCT GGG GGA GGC TTA GTG AAG CCT GGA GGG TCC CTG AAA CTC TCC
 V   K   L   V   E   S   G   G   G   L   V   K   P   G   G   S   L   K   L   S 150                    180
TGT GCA GCC TCT GGA TTC ACT TTC AGT GCA TAT ACC TAT GCC ATG TCT TGG GTT CGC CAG
 C   A   A   S   G   F   T   F   S   A   Y   T   Y   A   M   S   W   V   R   Q
                                                      —————————
                                                             210                    240
ACT CCA GAG AAG AGG CTG GAG TGG GTC GCA TCC ATT AGT ACT GGT GGT AGC ACC TAC TAT
 T   P   E   K   R   L   E   W   V   A   S   I   S   T   G   G   S   T   Y   Y
                                              —————————————————————————————————

270                    300
CCA GAC AGT GTG AAG GGC CGA TTC ACC ATC TCC AGA GAT AAT GCC AGG AAC ATC CTG TAC
 P   D   S   V   K   G   R   F   T   I   S   R   D   N   A   R   N   I   L   Y
—————————

330                    360
CTG CAA ATG AGC AGT CTG AGG TCT GAG GAC ACG GCC ATG TAT TAC TGT GCA AGA GAC TAT GAC GGG
 L   Q   M   S   S   L   R   S   E   D   T   A   M   Y   Y   C   A   R   D   Y   D   G
                                                                          ———————————————

390
TAT TTT GAC TAC TGG GGC CAA GGC ACC ACT CTC ACA GTC TCC TCA
 Y   F   D   Y   W   G   Q   G   T   T   L   T   V   S   S
———————————————
```

```
ATG GAG ACA GAC ACA ATC CTG CTA TGG GTG CTG CTG CTC TGG GTT CCA GGC TCC ACT GGT
 M   E   T   D   T   I   L   L   W   V   L   L   L   W   V   P   G   S   T   G       60

GAC ATT CAG ATG ACC CAA TCT CCG AGC TCT TTG TCT GCG TCT GTA GGG GAT AGG GTC ACT
 D   I   Q   M   T   Q   S   P   S   S   L   S   A   S   V   G   D   R   V   T      120
 =

ATC ACC TGC AAG GCC AGC CAA AGT GTT GAT TAT GAT GGT GAT AGT TAT ATG AAC TGG TAC
 I   T   C   K   A   S   Q   S   V   D   Y   D   G   D   S   Y   M   N   W   Y      180
         _____

CAA CAG AAA CCA GGA AAG GCA CCC AAG CTT CTC ATC TAT GCT GCA TCC AAC CTA GAA TCT
 Q   Q   K   P   G   K   A   P   K   L   L   I   Y   A   A   S   N   L   E   S      240
                                                         _____

GGT ATC CCA TCC AGG TTT AGT GGC AGT GGG TCT GGG ACA GAC TTC ACC CTC ACC ATC TCT
 G   I   P   S   R   F   S   G   S   G   S   G   T   D   F   T   L   T   I   S      300

TCT CTG CAG CCG GAG GAT TTC GCA ACC TAT TAC TGT CAG CAA AGT AAT GAA GAT CCG TGG
 S   L   Q   P   E   D   F   A   T   Y   Y   C   Q   Q   S   N   E   D   P   W      360
                                                 _____

ACG TTC GGT CAA GGC ACC AAG GTG GAA ATC AAA
 T   F   G   Q   G   T   K   V   E   I   K                                           390
 _
```

FIG. 7A

```
ATG AAC TTC GGG TCC AGC TTG ATT TTC CTT GTC CTT GTT TTA AAA GGT GTC CAG TGT GAA    60
 M   N   F   G   S   S   L   I   F   L   V   L   V   L   K   G   V   Q   C   E

GTG CAA CTG GTG GAG TCT GGG GGA GGC TTA GTG CAG CCT GGA GGA AGC TTG AGA CTC TCC   120
 V   Q   L   V   E   S   G   G   G   L   V   Q   P   G   G   S   L   R   L   S

TGT GCA GCC TCT GGA TTC ACT TTC AGT GCA TAC GCC ATG TCT TGG GTT CGC CAG GCT CCA   180
 C   A   A   S   G   F   T   F   S   A   Y   A   M   S   W   V   R   Q   A   P
                                         T   Y   A   M   S

GGG AAG GGA CTC GAG TGG GTC GCA TCC ATT AGT ACT GGT GGT AGC ACC TAC TAT CCA GAC   240
 G   K   G   L   E   W   V   A   S   I   S   T   G   G   S   T   Y   Y   P   D
                                 S   I   S   T   G   G   S   T   Y   Y   P   D

AGT GTG AAG GGC CGA TTC ACC ATC TCC AGA GAT AAT GCC AAG AAC ACC CTG TAC CTG CAA   300
 S   V   K   G   R   F   T   I   S   R   D   N   A   K   N   T   L   Y   L   Q
 S   V   K   G

ATG AAT TCT CTG AGG GCT GAG GAC ACG GCC GTG TAT TAC TGT GCA AGA GAC TAT GAC GGG   360
 M   N   S   L   R   A   E   D   T   A   V   Y   Y   C   A   R   D   Y   D   G
                                                         A   R   D   Y   D   G

TAT TTT GAC TAC TGG GGC CAA GGG ACC CTG GTC ACA GTC TCC TCA                       
 Y   F   D   Y   W   G   Q   G   T   L   V   T   V   S   S
 Y   F   D   Y
```

FIG. 7B

HUMANIZED ANTIBODIES REACTIVE WITH L-SELECTIN

REFERENCE TO RELATED INVENTIONS

This application is a continuation-in-part of U.S. Ser. No. 08/160,074, filed Nov. 30, 1993 now abandoned, which is a continuation-in-part of U.S. Ser. No. 07/983,946, filed Dec. 1, 1992 now abandoned. This application also derives priority from EP 95 112 895.8, filed Aug. 17, 1995, and EP 95 114 696.8, filed Sep. 19, 1995. All of the prior U.S. and foreign applications from which priority is derived are incorporated by reference in their entirety for all purposes.

FIELD OF THE INVENTION

The present invention relates generally to the combination of recombinant DNA and monoclonal antibody technologies for developing novel biologics and, more particularly, for example, to the production of non-immunogenic (in humans) immunoglobulins specific for the L-selectin protein and their uses in vitro and in vivo.

BACKGROUND OF THE INVENTION

The ability of cells to adhere to one another plays a critical role in development, normal physiology, and disease processes. This ability is mediated by adhesion molecules, generally glycoproteins, expressed on cell membranes. Often, an adhesion molecule on one cell type will bind to another adhesion molecule expressed on a different cell type, forming a receptor counter-receptor pair. Three very important classes of adhesion molecules are the integrins, selecting, and immunoglobulin (Ig) superfamily members (see Springer, *Nature* 346:425 (1990); Osborn, *Cell* 62:3 (1990); Hynes, *Cell* 69:11 (1992), all of which are incorporated herein by reference in their entirety for all purposes). These molecules are especially vital to the interaction of leukocytes and platelets with themselves and with the extracellular matrix and vascular endothelium.

Integrins are heterodimeric transmembrane glycoproteins consisting of an α chain (120–180 kD) and a β chain (90–110 kD), generally having short cytoplasmic domains. The α subunits all share sequence homology and motifs with each other, as do the β subunits. The three known integrins containing the β subunit designated $\beta_2$ are important to the function of T cells, neutrophils and monocytes. LFA-1 ($\alpha_L\beta_2$) is widely distributed on lymphocytes, granulocytes and monocytes. Its counter-receptor is ICAM-1 (and perhaps of lesser importance, ICAM-2) an Ig family molecule which is expressed on many cells including leukocytes and is up-regulated on vascular endothelium by cytokines such as TNF and IL-1. Blocking LFA-1 on T cells with antibodies to either the α or β subunit strongly inhibits adhesion-dependent functions such as CTL-mediated lysis of target cells. Mac-1 ($\alpha_M\beta_2$) is distributed on neutrophils and monocytes, and its counter-receptor is also ICAM-1 (and possibly ICAM-2). Among other things, Mac-1 is the type 3 complement receptor (CR3) and binds the C3bi fragment. The third $\beta_2$ integrin, P150,95 ($\alpha_X\beta_2$), is also found on neutrophils and monocytes, but seems of less importance. The a subunits of LFA-1, Mac-1 and P150,95 are also given the respective CD designations CD11a, CD11b and CD11c, while $\beta_2$ is also denoted CD18, so that LFA-1 is CD11a/CD18 and Mac-1 is CD11b/CD18.

There are three known selectins, which were previously known as LECCAMs, and are now designated L-selectin (also called LECAM-1, Mel-14 or LAM-1), E-selectin (also called ELAM-1) and P-selectin (also called GMP140 or PADGEM). They have all been sequenced at the cDNA level and share sequence homology and motifs, including a lectin-like domain. L-selectin has a dual role: it is a homing receptor on T cells for the high endothelial venules of peripheral lymph nodes, and it is an adhesion molecule on neutrophils for endothelium (Hallmann et al., *Biochem. Biophys. Res. Commun.* 174:236 (1991), which is incorporated herein by reference in its entirety for all purposes). E-selectin and P-selectin are both induced on endothelium by cytokines, although with different kinetics. L-selectin is a counter-receptor on neutrophils for both E-selectin and P-selectin (Picker et al., *Cell* 66:921 (1991), which is incorporated herein by reference in its entirety for all purposes), although all three selectins probably have other counter-receptors as well. In particular, E-selectin binds the carbohydrate group sialyl Lewis x (sLex) (Lowe et al., *Cell* 63:475 (1990)), which is incorporated herein by reference in its entirety for all purposes), and while this carbohydrate is prominently presented on L-selectin (Picker et al., *Cell* 66:921 (1991)), it may occur on other proteins as well. E-selectin is expressed especially in cutaneous sites of inflammation and also serves as an adhesion molecule for skin-homing T cells that may contribute to the inflammation (Picker et al., *Nature* 349:796 (1991), which is incorporated herein by reference in its entirety for all purposes).

In various assays, antibodies to CD11a, CD11b, CD18, L-selectin and E-selectin all block binding of neutrophils to activated endothelial cells to a lessor or greater degree, but the most complete inhibition is generally achieved by the combination of an antibody to CD18 and an antibody to L- or E-selectin (see, e.g., Luscinskas, *J. Immunol.* 142:2257 (1989)), which is incorporated herein by reference in its entirety for all purposes). A recent but now widely accepted model accounts for these facts with a three step process of adhesion (Butcher, *Cell* 67:1033 (1991), which is incorporated herein by reference in its entirety for all purposes). In the first step, neutrophils reversibly bind to inflamed vascular endothelium via the selecting, which bind well under conditions of flow, causing the neutrophils literally to roll along the vascular wall. The neutrophils are then activated by a variety of stimulants surrounding or released by the endothelium, including IL-8, PAF and C5a. The activated neutrophils shed L-selectin and up-regulate Mac-1. In the final step, binding of Mac-1 to ICAM-1 and perhaps other counter-receptors on the endothelial cells allows stable adhesion and extravasation through the endothelium.

In principle, antibodies or other antagonists of the integrin and selectin adhesion molecules could abort this process, by preventing neutrophils from binding to endothelium and from extravasating into tissues. Hence such antibodies could be used to treat a great many different disease conditions of which inflammation is an important component.

For example, in animal models anti-CD18 antibodies, which bind to both LFA-1 and Mac-1, have been useful in reducing ischemia-reperfusion injury (see, e.g., Vedder et al., *J. Clin. Invest.* 81:939 (1988); Vedder et al., *Proc. Natl. Acad. Sci. USA* 87:2643 (1990); U.S. Pat. No. 4,797,277). They also reduce neutrophil-mediated damage in the lung in response to various insults (Doerschuk et al., *J. Immunol.* 144:2327 (1990) and Mulligan et al., *J. Immunol.* 148:1847 (1992)), including gram-negative sepsis (Walsh et al., *Surgery* 110:205 (1991)). In a rabbit model, anti-CD18 antibodies also protect from lethality due to meningitis (Tuomanen et al., *J. Exp. Med.* 170:959 (1990)). They may also be useful in preventing or treating organ transplant rejection because-they block T-cell function.

For example, injection of antibodies to L-selectin or E-selectin into rodents suppressed neutrophil accumulation within inflamed peritoneum (Jutila et al., *J. Immunol.* 143:3318 (1989) and Mulligan et al., *J. Clin. Invest.* 88:1396 (1991)). Intravital video microscopy revealed that an anti-L-selectin antibody strongly inhibits rolling of leukocytes along the vascular wall endothelium of mesenteric venules exteriorized from rabbits (von Adrian et al., *Proc. Natl. Acad. Sci. USA* 88:7538 (1991)). An anti-E-selectin antibody greatly reduced vascular injury induced by immune complex deposition in the skin or lungs of rats, and substantially reduced neutrophil accumulation at those sites (Mulligen et al., *J. Clin. Invest.* 88:1396 (1991)). Also, in a primate model of extrinsic asthma, an anti-E-selectin antibody greatly reduced neutrophil influx into the lung and associated late-phase airway obstruction after antigen inhalation (Gundel et al., *J. Clin. Invest.* 88:1407 (1991)).

Several antibodies including mouse DREG-55, mouse DREG-56 and mouse DREG-200 have been developed that bind to human L-selectin (Kishimoto et al., *Proc. Natl. Acad. Sci. USA* 87:2244 (1990), which is incorporated herein by reference in its entirety for all purposes). These antibodies partially or completely block the binding of human lymphocytes to peripheral lymph node high endothelial venules, and the binding of human neutrophils to stimulated human umbilical vein endothelial cells (Kishimoto et al., *Blood* 78:805 (1991), which is incorporated herein by reference in its entirety for all purposes). The capacity of these antibodies to block binding of neutrophils to endothelial cells indicates that the antigen to which they bind, L-selectin, may be an appropriate target for potential therapeutic agents.

Unfortunately, the use of non-human monoclonal antibodies such as mouse DREG-200 have certain drawbacks in human treatment, particularly in repeated therapeutic regimens as explained below. Mouse monoclonal antibodies, for example, have a relatively short circulating half-life, and lack other important immunoglobulin functional characteristics when used in humans.

Perhaps more importantly, non-human monoclonal antibodies contain substantial stretches of amino acid sequences that will be immunogenic when injected into a human patient. Numerous studies have shown that, after injection of a foreign antibody, the immune response elicited by a patient against an antibody can be quite strong, essentially eliminating the antibody's therapeutic utility after an initial treatment. Moreover, as increasing numbers of different mouse or other antigenic (to humans) monoclonal antibodies can be expected to be developed to treat various diseases, after the first or several treatments with any different non-human antibodies, subsequent treatments even for unrelated therapies can be ineffective or even dangerous in themselves, because of cross-reactivity. While the production of so-called "chimeric antibodies" (e.g., mouse variable regions joined to human constant regions) has proven somewhat successful, a significant immunogenicity problem remains.

To attempt to overcome immunogenicity problems several examples of humanized antibodies have been produced. The transition from a murine to a humanized antibody involves a compromise of competing considerations, the solution to which varies for different antibodies. To minimize immunogenicity, the immunoglobulin should retain as much of the human acceptor sequence as possible. However, to retain authentic binding properties, the immunoglobulin framework should contain sufficient substitutions of the human acceptor sequence to ensure a three-dimensional conformation of CDR regions as close as possible to that in the mouse donor immunoglobulin. As a result of these competing considerations, many humanized antibodies produced to-date show significant loss of binding affinity compared with corresponding murine antibodies. See, e.g., Jones et al., *Nature* 321:522–525 (1986); Shearman et al., *J. Immunol.* 147:4366–4373 (1991); Kettleborough Protein Engineering 4:773–783 (1991); Gorman et al., *Proc. Natl. Acad. Sci. USA* 88:4181–4185 (1991); Tempest et al., *Biotechnology* 9:266–271 (1991); Riechmann et al., *Nature* 332:323 (1988) and EPO Publication No. 0239400) (each of which is hereby by reference in its entirety for all purposes).

Thus, there is a need for improved forms of humanized immunoglobulins specific for L-selectin antigen that are substantially non-immunogenic in humans, yet easily and economically produced in a manner suitable for therapeutic formulation and other uses. The present invention fulfills these and other needs.

SUMMARY OF THE INVENTION

The present invention provides novel compositions useful, for example, in the treatment of inflammatory human disorders, the compositions containing humanized immunoglobulins specifically capable of binding to L-selectin. The immunoglobulins can have two pairs of light chain/heavy chain complexes, at least one chain comprising one or more mouse complementarity determining regions functionally joined to human framework region segments. For example, mouse complementarity determining regions, with or without additional naturally-associated mouse amino acid residues, can be introduced into human framework regions to produce humanized immunoglobulins capable of binding to the L-selectin at affinity levels stronger than about $10^7$ $M^{-1}$. These humanized immunoglobulins will also be capable of blocking the binding of the CDR-donating mouse monoclonal antibody to L-selectin.

The immunoglobulins, including binding fragments and other derivatives thereof, of the present invention may be produced readily by a variety of recombinant DNA techniques, with ultimate expression in transfected cells, preferably immortalized eukaryotic cells, such as myeloma or hybridoma cells. Polynucleotides comprising a first sequence coding for humanized immunoglobulin framework regions and a second sequence set coding for the desired immunoglobulin complementarity determining regions can be produced synthetically or by combining appropriate cDNA and genomic DNA segments.

The humanized immunoglobulins may be utilized alone in substantially pure form, or together with a chemotherapeutic agent such as a non-steroidal anti-inflammatory drug (e.g., aspirin), a corticosteroid, or an immunosuppressant. All of these compounds will be particularly useful in treating inflammatory disorders. The humanized immunoglobulins or their complexes can be prepared in a pharmaceutically acceptable dosage form, which will vary depending on the mode of administration.

BRIEF DESCRIPTION OF THE FIGURES

FIG. 1. Sequences of the cDNA and translated amino acid sequences of the light chain (A) (SEQ ID NOS:1 and 2) and heavy chain (B) (SEQ ID NOS:3 and 4) variable regions of the mouse DREG-200 antibody. The mature heavy chain begins with amino acid 20 E, and the mature light chain begins with amino acid 21 D, preceded by the respective signal sequences.

FIG. 2. Amino acid sequences of the mature light chain (A) (SEQ ID NOS:5 and 6) and heavy chain (B) (SEQ ID NOS:7 and 8) variable regions of the mouse DREG-200 antibody (upper lines) and humanized DREG-200 antibody (lower lines). The three CDRs in each chain are underlined. Residues in the framework that have been replaced with mouse amino acids or typical human amino acids in the humanized antibody are double underlined.

FIG. 3. Nucleotide sequences of the genes encoding the light chain (A) (SEQ ID NOS:9 and 10) and heavy chain (B) (SEQ ID NOS:11 and 12) variable regions of the humanized DREG-200 antibody, beginning and ending with the XbaI sites, and translated amino acid sequences, including signal sequences.

FIGS. 6A and 6B: Sequences of the cDNA and translated amino acid sequence of the light chain (A) (SEQ ID NOS:13 and 14) and heavy chain (B) (SEQ ID NOS:15 and 16) variable regions of the DREG-55 antibody. The first amino acid of each mature chain is indicated by a double underline and preceded by the respective signal sequences. The three CDRs in each chain are underlined.

FIGS. 7A and 7B: Sequences of the synthetic DNA and translated amino acid sequences of the light chain (A) (SEQ ID NOS:17 and 18) and heavy chain (B) (SEQ ID NOS:19 and 20) variable regions of the humanized DREG-55 antibody (HuDREG-55). The first amino acid of each mature chain is indicated by a double underline and preceded by the respective signal sequences. The three CDRs in each chain are underlined.

DEFINITIONS

Figure 4:
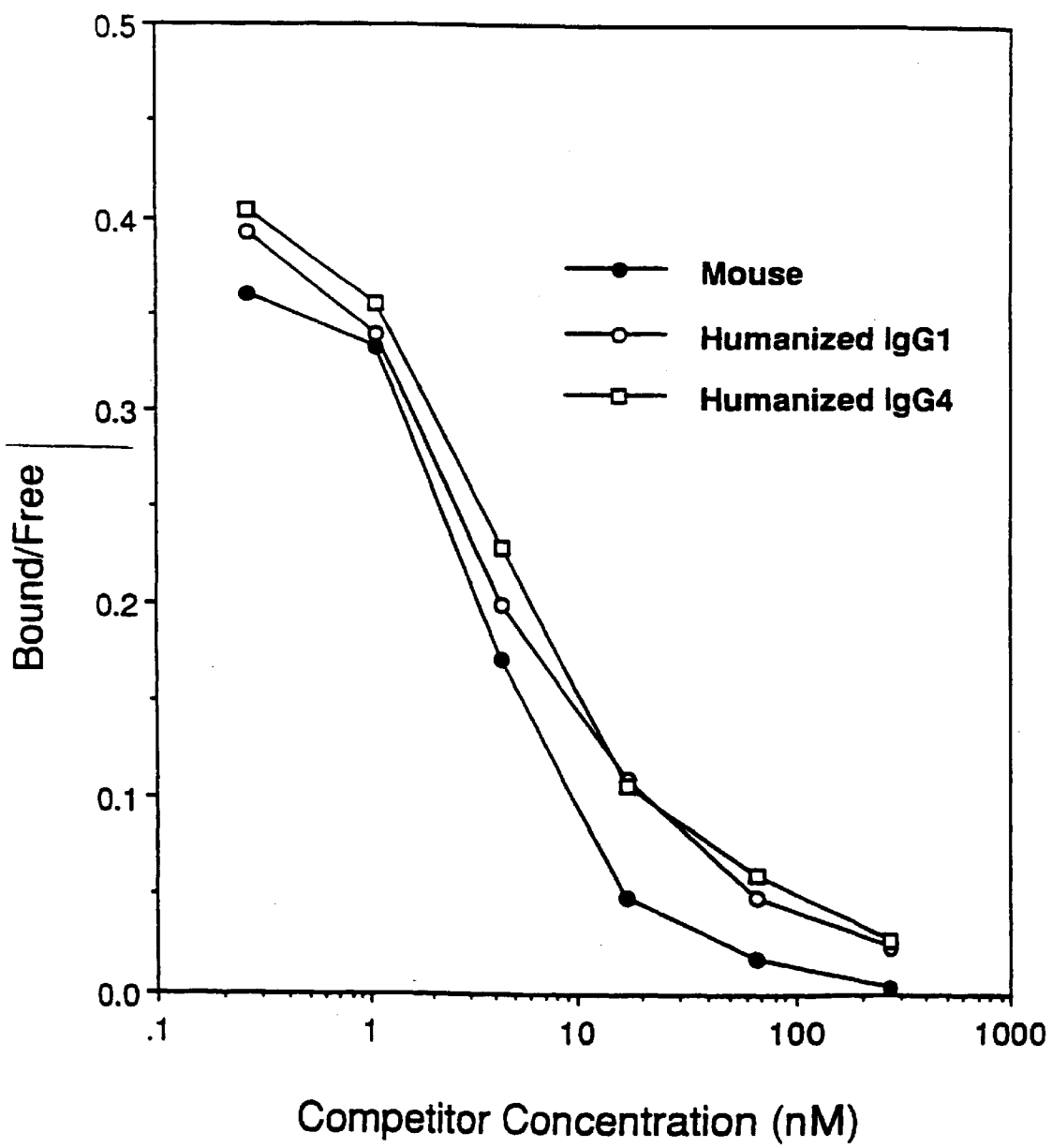
FIG. 4. Competitive binding of mouse and humanized IgG1 and IgG4 DREG-200 antibodies. The target cells were L2-1 cells, a mouse pre-B cell line, that was transfected with a human L-selectin gene and thus expresses human L-selectin (Berg et al., *Biochem. Biophys. Res. Comm.* 184:1048 (1992)). $5 \times 10^5$ cells were incubated with 3 ng of $^{125}$I-labeled tracer mouse antibody (2 $\mu$Ci/$\mu$g), together with increasing amounts of mouse or humanized competitor antibody as indicated in 0.2 ml of binding buffer (PBS+2% FBS+0.1% azide) for 1 hr at 4° C. Cells were washed and pelleted, and their bound radioactivity measured. The concentrations of bound and free tracer antibody were calculated.

The term "substantial identity" or "substantial homology" means that two peptide sequences, when optimally aligned, such as by the programs GAP or BESTFIT using default gap weights, share at least 65 percent sequence identity, preferably at least 80 or 90 percent sequence identity, more preferably at least 95 percent sequence identity or more (e.g., 99 percent sequence identity). Preferably, residue positions which are not identical differ by conservative amino acid substitutions.

For purposes of classifying amino acids substitutions as conservative or nonconservative, amino acids are grouped as follows: Group I (hydrophobic sidechains): norleucine, met, ala, val, leu, ile; Group II (neutral hydrophilic side chains): cys, ser, thr; Group III (acidic side chains): asp, glu; Group IV (basic side chains): asn, gin, his, lys, arg; Group V (residues influencing chain orientation): gly, pro; and Group VI (aromatic side chains): trp, tyr, phe. Conservative substitutions involve substitutions between amino acids in the same class. Nonconservative substitutions constitute exchanging a member of one of these classes for a member of another.

Amino acids from the variable regions of the mature heavy and light chains of immunoglobulins are designated Hx and Lx respectively, where x is a number designating the position of an amino acids according to the scheme of Kabat, *Sequences of Proteins of Immunological Interest* (National Institutes of Health, Bethesda, Md., 1987 and 1991). Kabat lists many amino acid sequences for antibodies for each subclass, and lists the most commonly occurring amino acid for each residue position in that subclass. Kabat uses a method for assigning a residue number to each amino acid in a listed sequence, and this method for assigning residue numbers has become standard in the field. Kabat's scheme is extendible to other antibodies not included in his compendium by aligning the antibody in question with one of the consensus sequences in Kabat. The use of the Kabat numbering system readily identifies amino acids at equivalent positions in different antibodies. For example, an amino acid at the L50 position of a human antibody occupies the equivalent position to an amino acid position L50 of a mouse antibody.

From N-terminal to C-terminal, both light and heavy chains comprise the domains FR1, CDR1, FR2, CDR2, FR3, CDR3 and FR4. The assignment of amino acids to each domain is in accordance with the definitions of Kabat (1987) and (1991), supra, or Chothia & Lesk, *J. Mol. Biol.* 196:901–917 (1987); Chothia et al., *Nature* 342:878–883 (1989).

DETAILED DESCRIPTION OF THE INVENTION

Generally, the nomenclature used hereafter and the laboratory procedures in cell culture, molecular genetics, and nucleic acid chemistry and hybridization described below are those well known and commonly employed in the art. Standard techniques are used for recombinant nucleic acid methods, polynucleotide synthesis, cell culture, and transgene incorporation (e.g., electroporation, microinjection, lipofection). Generally enzymatic reactions, oligonucleotide synthesis, and purification steps are performed according to the manufacturer's specifications. The techniques and procedures are generally performed according to conventional methods in the art and various general references which are provided throughout this document. The procedures therein are believed to be well known in the art and are provided for the convenience of the reader. All the information contained therein is incorporated herein by reference.

Humanized Antibodies Against L-Selectin

In accordance with the present invention, humanized immunoglobulins specifically reactive with L-selectin related epitopes are provided. These immunoglobulins usually have binding affinities to L-selectin of at least about $10^7$ $M^{-1}$, and preferably $10^8$ $M^{-1}$ to $10^9$ $M^{-1}$, $10^{10}$ $M^{-1}$ or stronger and, are capable of, e.g., binding to neutrophils. The humanized immunoglobulins will have a human framework and will have one or more complementarity determining regions (CDRS) from an immunoglobulin, typically a mouse immunoglobulin, specifically reactive with L-selectin. In a preferred embodiment, one or more of the CDRs will come from the mouse DREG-200 or DREG-55 antibody, and the humanized immunoglobulin will be of the IgG1 or IgG4 isotype. Thus, the immunoglobulins of the present invention, which can be produced economically in large quantities, find use, for example, in the treatment of inflammatory disorders in human patients by a variety of techniques.

The basic antibody structural unit is known to comprise a tetramer. Each tetramer is composed of two identical pairs of polypeptide chains, each pair having one "light" (about 25 kD) and one "heavy" chain (about 50–70 kD). The $NH_2$-terminus of each chain begins a variable region of about 100 to 110 or more amino acids primarily responsible for antigen recognition. The COOH part of each chain defines a constant region primarily responsible for effector function.

Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 more amino acids. (See, generally, *Fundamental Immunology*, Paul, W., Ed., Chapter 7, pp. 131–166, Raven Press, N.Y. (1984), which is incorporated herein by reference in its entirety for all purposes.)

The variable regions of each light/heavy chain pair form the antibody binding site. The chains all exhibit the same general structure of relatively conserved framework regions joined by three hypervariable regions, also called Complementarity Determining Regions or CDRs (see "Sequences of Proteins of Immunological Interest," Kabat, E., et al., U.S. Department of Health and Human Services (1987); and Chothia and Lesk, *J. Mol. Biol.*, 196:901–917 (1987), which are incorporated herein by reference in their entirety for all purposes). The CDRs from the two chains of each pair are aligned by the framework regions, enabling binding to a specific epitope.

As used herein, the term "immunoglobulin" refers to a protein consisting of one or more polypeptides substantially encoded by immunoglobulin genes. The recognized immunoglobulin genes include the kappa, lambda, alpha, gamma, delta, epsilon and mu constant region genes, as well as the myriad immunoglobulin variable region genes. The immunoglobulins may exist in a variety of forms besides antibodies; including, for example, Fv, Fab, and (Fab')$_2$ as well as bifunctional antibodies (e.g., Lanzavecchia et al., *Eur. J. Immunol.* 17:105 (1987)) and in single chains (e.g., Huston et al., *Proc. Natl. Acad. Sci. USA*, 85:5879–5883 (1988) and Bird et al., *Science*, 242:423–426 (1988), which are incorporated herein by reference in their entirety for all purposes). (See, generally, Hood et al., *Immunology* (Benjamin, N.Y., 2nd ed., 1984), Harlow & Lane, *Antibodies: A Laboratory Manual* (Cold Spring Harbor Laboratory, 1988) and Hunkapiller & Hood, *Nature*, 323:15–16 (1986), each of which are incorporated herein by reference in their entirety for all purposes).

Chimeric antibodies are antibodies whose light and heavy chain genes have been constructed, typically by genetic engineering, from immunoglobulin gene segments belonging to different species. For example, the variable (V) segments of the genes from a mouse monoclonal antibody may be joined to human constant (C) segments, such as $\gamma_1$ and $\gamma_4$. A typical therapeutic chimeric antibody is thus a hybrid protein consisting of the V or antigen-binding domain from a mouse antibody and the C or effector domain from a human antibody, although other mammalian species may be used.

As used herein, the term "framework region" refers to those portions of immunoglobulin light and heavy chain variable regions that are relatively conserved (i.e., other than the CDRs) among different immunoglobulins in a single species, as defined by Kabat, et al., supra. As used herein, a "human framework region" is a framework region that is substantially identical (about 85% or more) to the framework region of a naturally occurring human antibody or a consensus sequence of several such antibodies.

As used herein, the term "humanized immunoglobulin" refers to an immunoglobulin comprising a human framework, at least one CDR from a non-human antibody, and in which any constant region present is substantially identical to a human immunoglobulin constant region, i.e., at least about 85–90%, preferably at least 95% identical. Hence, all parts of a humanized immunoglobulin, except possibly the CDRs, are substantially identical to corresponding parts of one or more native human immunoglobulin sequences. For example, a humanized immunoglobulin would not encompass a chimeric mouse variable region/ human constant region antibody.

Humanized antibodies have at least three potential advantages over mouse, and in some cases chimeric antibodies, for use in human therapy:

1) because the effector portion is human, it may interact better with the other parts of the human immune system (e.g., destroy the target cells more efficiently by complement-dependent cytotoxicity (CDC) or antibody-dependent cellular cytotoxicity (ADCC)).

2) The human immune system should not recognize the framework or C region of the humanized antibody as foreign, and therefore the antibody response against such an injected antibody should be less than against a totally foreign mouse antibody or a partially foreign chimeric antibody.

3) Injected mouse antibodies have been reported to have a half-life in the human circulation much shorter than the half-life of normal antibodies (Shaw, D. et al., *J. Immunol.* 138:4534–4538 (1987)). Injected humanized antibodies will presumably have a half-life more like that of naturally occurring human antibodies, allowing smaller and less frequent doses to be given.

In one aspect, the present invention is directed to recombinant DNA segments encoding the heavy and/or light chain CDRs from an immunoglobulin capable of binding to a desired epitope of L-selectin, such as monoclonal antibodies mouse DREG-200, mouse DREG-55 or mouse DREG-56 (Kishimoto et al. (1990), supra, which is incorporated herein by reference in its entirety for all purposes). The DNA segments encoding these regions will typically be joined to DNA segments encoding appropriate human framework regions. Exemplary DNA sequences, which on expression code for the polypeptide chains comprising the heavy and light chain CDRs of monoclonal antibody mouse DREG-200 are included in FIG. 1. Due to codon degeneracy and non-critical amino-acid substitutions, other DNA sequences can be readily substituted for those sequences, as detailed below. For a detailed description of the design and production of humanized immunoglobulins, see commonly assigned Ser. Nos. 07/290,975 and 07/310,252, filed Dec. 28, 1988 and Feb. 13, 1989, respectively, both of which are incorporated herein by reference in their entirety for all purposes.

The DNA segments will typically further include an expression control DNA sequence operably linked to the humanized immunoglobulin coding sequences, including naturally-associated or heterologous promoter regions. Preferably, the expression control sequences will be eukaryotic promoter systems in vectors capable of transforming or transfecting eukaryotic host cells, but control sequences for prokaryotic hosts may also be used. Once the vector has been incorporated into the appropriate host, the host is maintained under conditions suitable for high level expression of the nucleotide sequences, and, as desired, the collection and purification of the light chains, heavy chains, light/heavy chain dimers or intact antibodies, binding fragments or other immunoglobulin forms may follow.

The nucleic acid sequences of the present invention capable of ultimately expressing the desired humanized antibodies can be formed from a variety of different polynucleotides (genomic or cDNA, RNA, synthetic oligonucleotides, etc.) and components (e.g., V, J, D, and C regions), as well as by a variety of different techniques. Joining appropriate genomic and synthetic sequences is presently the most common method of production, but cDNA sequences may also be utilized (see European Patent Publication No. 0239400 and Riechmann, L. et al., *Nature* 332:323–327 (1988), both of which are incorporated herein by reference in their entirety for all purposes).

Human constant region DNA sequences can be isolated in accordance with well known procedures from a variety of human cells, but preferably immortalized B-cells (see Kabat, supra, and WP87/02671). The CDRs for producing the immunoglobulins of the present invention will be similarly derived from monoclonal antibodies capable of binding to L-selectin and produced in any convenient mammalian source, including, mice, rats, rabbits, or other vertebrate capable of producing antibodies by well known methods. Suitable source cells for the DNA sequences and host cells for immunoglobulin expression and secretion can be obtained from a number of sources, such as the American Type Culture Collection (Catalogue of *Cell Lines and Hybridomas,* Fifth edition (1985) Rockville, Md., which is incorporated herein by reference in its entirety for all purposes). In preferred embodiments, the CDRs have sequences corresponding to the CDR sequences of mouse DREG-200, mouse DREG-55, or mouse DREG-56, respectively, and may include degenerate nucleotide sequences encoding the corresponding CDR amino acid sequence(s) of mouse DREG-200, mouse DREG-55, or mouse DREG-56.

In addition to the humanized immunoglobulins specifically described herein, other "substantially homologous" modified immunoglobulins can be readily designed and manufactured utilizing various recombinant DNA techniques well known to those skilled in the art. Other human antibodies than the Eu or Gal antibody discussed in the Examples can be used as a source of framework sequence. These framework sequences should exhibit a high degree of sequence identity with the mouse DREG-200 or DREG-55 variable region domains from which the CDRs were derived. The heavy and light chain variable framework regions can be derived from the same or different human antibody sequences. Indeed, the heavy and light chain framework regions can each be derived from more than one human antibody. The human antibody sequences can be the sequences of naturally occurring human antibodies or can be consensus sequences of several human antibodies. See Carter et al., WO 92/22653 (1992).

The unnatural juxtaposition of murine CDR regions with human variable framework region can result in unnatural conformational restraints, which, unless corrected by substitution of certain amino acid residues, lead to loss of binding affinity. The selection of amino acid residues for substitution is determined, in part, by computer modelling. Computer hardware and software for producing three-dimensional images of immunoglobulin molecules are widely available. In general, molecular models are produced starting from solved structures for immunoglobulin chains or domains thereof. The chains to be modelled are compared for amino acid sequence similarity with chains or domains of solved three dimensional structures, and the chains or domains showing the greatest sequence similarity is/are selected as starting points for construction of the molecular model. The solved starting structures are modified to allow for difference between the actual amino acids in the immunoglobulin chains or domains being modelled, and those in the starting structure. The modified structures are then assembled into a composite immunoglobulin. Finally, the model is refined by energy minimization and by verifying that all atoms are within appropriate distances from one another and that bond lengths and angles are within chemically acceptable limits. Example 2 discusses in more detail the steps taken to produce a three dimensional computer model for the variable regions of the mouse DREG-200 antibody. This model can in turn serve as a starting point for predicting the three-dimensional structure of an antibody containing the mouse DREG-200 complementarity determining regions substituted in human framework structures. Additional models can be constructed representing the structure when further amino acid substitutions, to be discussed infra, are introduced.

In general, substitution of human amino acid residues with murine should be minimized, because introduction of murine residues increases the risk of the antibody eliciting a HAMA response in humans. Amino acids are selected for substitution based on their possible influence on CDR conformation and/or binding to antigen. Investigation of such possible influences is by modelling, examination of the characteristics of the amino acids at particular locations, or empirical observation of the effects of substitution or mutagenesis of particular amino acids.

When an amino acid differs between a mouse DREG-200 variable framework region and an equivalent human variable framework region, the human framework amino acid should usually be substituted by the equivalent mouse amino acid if it is reasonably expected that the amino acid:

(1) noncovalently contacts antigen directly, or
(2) is adjacent to a CDR region or otherwise interacts with a CDR region (e.g., is within about 4–6 Å of a CDR region).

Other candidates for substitution are acceptor human framework amino acids that are unusual for a human immunoglobulin at that position (e.g., amino acid H113 of human Eu antibody). These amino acids can be substituted with amino acids from the equivalent position of more typical human immunoglobulins. Alternatively, amino acids from equivalent positions in the mouse DREG-200 can be introduced into the human framework regions when such amino acids are typical of human immunoglobulin at the equivalent positions.

In general, substitution of all or most of the amino acids fulfilling the above criteria is desirable. Occasionally, however, there is some ambiguity about whether a particular amino acid meets the above criteria, and alternative variant immunoglobulins are produced, one of which has that particular substitution, the other of which does not. The humanized antibodies of the present invention will usually contain a substitution with a mouse light chain framework residue with a corresponding mouse DREG-200 residue in at least 1, 2, 3, 4 and more usually 5, of the following positions: L87, L54, L66, L76 and L93. The humanized antibodies also usually contain a substitution with a mouse heavy chain framework residue in at least 1, 3, 5, 7, 9, 10, 11 and, more usually 12 of the following positions: H93, H95, H98, H111, H112, H115, H30, H98, H111, H27, H48, and H72. In preferred embodiments when the human heavy chain acceptor immunoglobulin is Eu, the heavy chain also contains a substitution at H113. This position is usually substituted with the amino acid from the equivalent position of a human immunoglobulin having a more typical amino acid residues.

Usually the CDR regions in humanized antibodies are substantially identical, and more usually, identical to the corresponding CDR regions in the mouse DREG-200 antibody. Occasionally, however, it is desirable to change one of the residues in a CDR region, for example, to create a resemblance to the binding site of a ligand of L-selectin Although not usually desirable, it is sometimes possible to make one or more conservative amino acid substitutions of CDR residues without appreciably affecting the binding affinity of the resulting humanized immunoglobulin.

Other than for the specific amino acid substitutions discussed above, the framework regions of humanized immunoglobulins are usually substantially identical, and more usually, identical to the framework regions of the human antibodies from which they were derived. However, in some embodiments the framework regions can vary from the native sequences at the primary structure level by several amino acid substitutions, terminal and intermediate additions and deletions, and the like. Stereoisomers (e.g., D-amino acids) of the twenty conventional amino acids, unnatural amino acids such as $\alpha,\alpha$-disubstituted amino acids, N-alkyl amino acids, lactic acid, and other unconventional amino acids may also be suitable components for polypeptides of the present invention. Of course, many of the amino acids in the framework region make little or no direct contribution to the specificity or affinity of an antibody. Thus, many individual conservative substitutions of framework residues can be tolerated without appreciable change of the specificity or affinity of the resulting humanized immunoglobulin. However, in general, such substitutions are undesirable. Modifications of the genes may be readily accomplished by a variety of well-known techniques, such as site-directed mutagenesis (see Gillman & Smith, *Gene* 8:81–97 (1979) and Roberts et al., *Nature* 328:731–734 (1987), both of which are incorporated herein by reference in their entirety for all purposes).

Alternatively, polypeptide fragments comprising only a portion of the primary antibody structure may be produced, which fragments possess one or more immunoglobulin activities (e.g., binding activity). These polypeptide fragments may be produced by proteolytic cleavage of intact antibodies by methods well known in the art, or by inserting stop codons at the desired locations in the vectors pVk and pVg1-dhfr using site-directed mutagenesis, such as after CH1 to produce Fab fragments or after the hinge region to produce (Fab')$_2$ fragments. Single chain antibodies may be produced by joining VL and VH with a DNA linker (see Huston et al., supra, and Bird et al., supra). As one example, Fv or Fab fragments may be produced in *E. coli* according to the methods of Buchner and Rudolph, *Bio/Technology* 9:157–162 (1991) and Skerra et al., *Bio/Technology* 9:273–277 (1991), incorporated herein by reference in their entirety for all purposes. Fv and Fab may also be produced by expression of encoding polynucleotides in eukaryotic, preferably mammalian, cells. Also because like many genes, the immunoglobulin-related genes contain separate functional regions, each having one or more distinct biological activities, the genes may be fused to functional regions from other genes (e.g., enzymes, see commonly assigned U.S. Ser. No. 132,387, filed Dec. 15, 1987, which is incorporated herein by reference in its entirety for all purposes) to produce fusion proteins (e.g., immunotoxins) having novel properties.

Expression of the humanized immunoglobulin sequences in bacterial hosts may be used to advantage to select higher affinity humanized immunoglobulin sequences by mutagenizing the CDR regions and producing bacteriophage display libraries which may be screened for humanized immunoglobulin CDR variants which possess high affinity and/or high specificity binding to L-selectin. One potential advantage of such affinity sharpening is the generation of humanized immunoglobulin CDR variants which have improved binding affinity and/or reduced cross-reactivity with molecules other than L-selectins. Methods for producing phage display libraries having immunoglobulin variable region sequences are provided in the art, for example, see Cesareni, *FEBS Lett* 307:66–70 (1992); Swimmer et al., *Proc. Natl. Acad. Sci. USA* 89:3756–60 (1992); Gram et al., *Proc. Natl. Acad. Sci. USA* 89:3576–80 (1992); Clackson et al., *Nature* 352:624–8 (1991); Scott & Smith, *Science* 249:386–90 (1990); Garrard et al., *Bio/Techniques* 9:1373–1377 (1991), which are incorporated herein by reference in their entirety for all purposes. The resultant affinity sharpened CDR variant humanized immunoglobulin sequences are subsequently expressed in a suitable host for efficient expression.

As stated previously, the DNA sequences will be expressed in hosts after the sequences have been operably linked to (i.e., positioned to ensure the functioning of) an expression control sequence. These expression vectors are typically replicable in the host organisms either as episomes or as an integral part of the host chromosomal DNA. Commonly, expression vectors will contain selection markers, e.g., tetracycline-resistance (tet$^R$), G418-resistance (neo$^R$), mycophenolic acid-resistance (gpt), or HSV-tk, to permit detection of those cells transformed with the desired DNA sequences (see, e.g., U.S. Pat. No. 4,704,362, which is incorporated herein by reference in its entirety for all purposes).

*E. coli* is one prokaryotic host useful particularly for cloning the DNA sequences of the present invention. Other microbial hosts suitable for use include bacilli, such as Bacillus subtilis, and other enterobacteriaceae, such as Salmonella, Serratia, and various Pseudomonas species. In these prokaryotic hosts, one can also make expression vectors, which will typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters will typically control expression, optionally with an operator sequence, and have ribosome binding site sequences and the like, for initiating and completing transcription and translation.

Other microbes, such as yeast, may also be used for expression. Saccharomyces is a preferred host, with suitable vectors having expression control sequences, such as promoters, including 3-phosphoglycerate kinase or other glycolytic enzymes, and an origin of replication, termination sequences and the like as desired.

Plants and plant cell cultures may be used for expression of the humanized immunoglobulins of the invention. (Larrick & Fry, *Hum. Antibodies Hybridomas* 2(4):172–89 (1991); Benvenuto et al., *Plant Mol. Biol.* 17(4):865–74 (1991); Durin et al., *Plant Mol. Biol.* 15(2):281–93 (1990); Hiatt et al., *Nature* 342:76–8 (1989), incorporated herein by reference in their entirety for all purposes). Preferable plant hosts include, for example: Arabidopsis, *Nicotiana tabacum, Nicotiana rustica,* and *Solanum tuberosum.* A preferred expression cassette for expressing polynucleotide sequences encoding the humanized anti-L-selectin antibodies of the invention is the plasmid pMOG18 in which the inserted polynucleotide sequence encoding the humanized immunoglobulin chain is operably linked to a CaMV 35S promoter with a duplicated enhancer; pMOG18 is used according to the method of Sijmons et al., *Bio/Technology* 8:217–221 (1990), incorporated herein by reference in its entirety for all purposes. Alternatively, a preferred embodiment for the expression of humanized immunoglobulins in plants follows the methods of Hiatt et al., supra, with the substitution of polynucleotide sequences encoding the humanized anti-L-selectin antibodies of the invention for the immunoglobulin sequences used by Hiatt et al., supra. *Agrobacterium tumifaciens* T-DNA-based vectors may also be used for expressing humanized immunoglobulin sequences, preferably such vectors include a marker gene encoding spectinomycin-resistance or other selectable marker.

Insect cell culture may also be used to produce the humanized immunoglobulins of the invention, typically using a baculovirus-based expression system. The humanized immunoglobulins may be produced by expressing polynucleotide sequences encoding the humanized immunoglobulins according to the methods of Putlitz et al., *Bio/Technology* 8:651–654 (1990), incorporated herein by reference in its entirety for all purposes. The method of Putlitz et al. can be followed with the modification that polynucleotide sequences encoding the humanized anti-L-selectin antibodies of the invention are inserted in place of the mouse monoclonal Ab 6A4 heavy chain and light chain cDNA sequences of Putlitz et al.

In addition to microorganisms and plants, mammalian tissue cell culture may also be used to express and produce the polypeptides of the present invention (see Winnacker, *From Genes to Clones* (VCH Publishers, NY, 1987), which is incorporated herein by reference in its entirety for all purposes). Mammalian cells are actually preferred, because a number of suitable host cell lines capable of secreting intact immunoglobulins have been developed in the art, and include the CHO cell lines, various COS cell lines, HeLa cells, preferably myeloma cell lines, etc, or transformed B-cells or hybridomas. Expression vectors for these cells can include expression control sequences, such as an origin of replication, a promoter, an enhancer (Queen et al., *Immunol. Rev.* 89:49–68 (1986), which is incorporated herein by reference in its entirety for all purposes), and necessary processing information sites, such as ribosome binding sites, RNA splice sites, polyadenylation sites, and transcriptional terminator sequences. Preferred expression control sequences are promoters derived from immunoglobulin genes, SV40, Adenovirus, Bovine Papilloma Virus, cytomegalovirus and the like. Generally, a selectable marker, such as a $neo^R$ expression cassette, is included in the expression vector.

Mammalian cell lines expressing humanized antibodies are preferably cultured in serum-free media. For, example, the HUDREG-55 producing cell line may be readily grown in Serum-Free and Protein-Free Hybridoma Medium Cat. No. S-2897 from Sigma (St. Louis, Mo.). When the cell line is passaged in that medium, the level of production is essentially stable for at least 2 months. The cell line may also be grown in other serum-free media, for example Hybridoma-SFM Cat. No. 12045-076 from GibcoBRL (Gaithersburg, Md.).

Transgenes encoding a humanized immunoglobulin of the invention may be used to generate transgenic nonhuman animals which express the desired humanized immunoglobulin, typically in a recoverable body fluid such as milk or serum. Such transgenes comprise a polynucleotide sequence encoding the humanized immunoglobulin(s) operably linked to a promoter, usually with a linked enhancer, such as a rodent immunoglobulin enhancer or a casein gene promoter/enhancer (Buhler et al., *Bio/Technology* 8:140–143 (1990); Meade et al., *Bio/Technology* 8:443–446 (1990), incorporated herein by reference in its entirety for all purposes). Transgenes may be transferred into cells and embryos according to the methods described in the art and, infra, for homologous recombination constructs. Preferred nonhuman animals include: mice, rats, sheep, cows, and goats; with expression in bovine milk being particularly preferred. See WO91/08216 (1991) (which is incorporated in its entirety for all purposes). Purification of the humanized antibodies is accomplished by art-known purification methods for immunoglobulin purification.

The vectors containing the DNA segments of interest (e.g., the heavy and light chain encoding sequences and expression control sequences) can be transferred into the host cell by well-known methods, which vary depending on the type of cellular host. For example, calcium chloride transfection is commonly utilized for prokaryotic cells, whereas calcium phosphate treatment, lipofection, biolistics, viral-based transduction, or electroporation may be used for other cellular hosts. Tungsten particle ballistic transgenesis is preferred for plant cells and tissues. (See, generally, Maniatis et al., *Molecular Cloning: A Laboratory Manual* (Cold Spring Harbor Press, 1982), which is incorporated herein by reference in its entirety for all purposes.)

Once expressed, the whole antibodies, their diners, individual light and heavy chains, or other immunoglobulin forms of the present invention can be purified according to standard procedures of the art, including ammonium sulfate precipitation, affinity columns, column chromatography, gel electrophoresis and the like (see, generally, Scopes, R., *Protein Purification* (Springer-Verlag, N.Y., 1982), which is incorporated herein by reference in its entirety for all purposes). Substantially pure immunoglobulins of at least about 90 to 95% homogeneity are preferred, and 98 to 99% or more homogeneity most preferred, for pharmaceutical uses. Once purified, partially or to homogeneity as desired, the polypeptides may then be used therapeutically (including extracorporeally) or in developing and performing assay procedures, immunofluorescent stainings, and the like. (See, generally, *Immunological Methods,* Vols. I and II (Lefkovits and Pernis, eds., Academic Press, NY, 1979 and 1981).

In a preferred embodiment, humanized immunoglobulins are produced which bind to L-selectin with a binding affinity of at least $1\times10^7$ $M^{-1}$ in standard binding conditions (e.g., phosphate-buffered saline with 2 percent fetal bovine serum at 25° C.); one example of such humanized immunoglobulins is the humanized DREG-200 antibody comprising the amino acid sequences shown in FIG. 2. (Hereinafter, the humanized DREG-200 antibody is sometimes referred to as hu DREG-200.) Humanized immunoglobulins comprising the CDRs from mouse DREG-55 or from mouse DREG-56 also can bind to L-selectin with an affinity of at least $1\times10^7$ $M^{-1}$. The humanized antibodies of the invention preferably bind, in standard binding conditions, to human L-selectin with an affinity of at least $1\times10^8$ $M^{-1}$, more preferably with an affinity of at least $1\times10^9$ $M^{-1}$, and advantageously with an affinity of at least $1\times10^{10}$ $M^{-1}$ or stronger. Usually, the binding affinity of a humanized immunoglobulin is within a factor of three, five or ten of the mouse immunoglobulin from which it was derived. For, example the affinity of the mouse DREG-200 antibody is about $10^8$ $M^{-1}$.

Computers

In another aspect of the invention, computers programmed to display three dimensional images of antibodies on a monitor are provided. For example, a Silicon Graphics IRIS 4D workstation running under the UNIX operating system and using the molecular modelling package QUANTA (Polygen Corp. USA) is suitable. Computers are useful for generating variants of humanized antibodies. In general, the antibodies of the invention already provide satisfactory binding affinity. However, it is likely that antibodies with even stronger binding affinity could be identified by further variation of certain amino acid residues. The three dimensional image will also identify many noncritical amino acids, which could be the subject of conservative substitutions without appreciable affecting the binding affinity of the antibody. Collectively even conservative substitutions can have a significant effect on the properties of an immunoglobulin. However, it is likely many individual conservative substitutions will not significantly impair the properties of the immunoglobulins.

Human Antibodies Against L-Selectin

In another aspect of the invention, human antibodies against L-selectin are provided. These antibodies are produced by a variety of techniques described below. Some human antibodies are selected by competitive binding experiments, or otherwise, to have the same epitope specificity as a particular mouse antibody, such as mouse DREG-200 or DREG-55 or a humanized version thereof. Such antibodies are particularly likely to share the useful therapeutic properties demonstrated for humanized DREG-200.

Antibodies having the required epitope specificity can also be identified by screening for the capacity to block neutrophil-endothelial cell interaction. A simple visual assay for detecting such interaction has been described by Kishimoto et al. (1991), supra. Briefly, monolayers of human umbilical vein cells are stimulated with IL-1. Neutrophils, with or without pretreatment with the antibody under test, are added to the monolayer under defined conditions, and the number of adhering neutrophils is determined microscopically. In one method, the neutrophils are obtained from human leukocyte adhesion deficient patients. See Anderson et al., *Ann. Rev. Med.* 38:175 (1987). The neutrophils from such patients lack integrin receptors, whose binding to neutrophils might obscure the effects of blocking L-selectin binding.

a. Trioma Methodology

The basic approach and an exemplary cell fusion partner, SPAZ-4, for use in this approach have been described by Oestberg et al., Hybridoma 2:361–367 (1983); Oestberg, U.S. Pat. No. 4,634,664; and Engleman et al., U.S. Pat. No. 4,634,666 (each of which is incorporated by reference in its entirety for all purposes). The antibody-producing cell lines obtained by this method are called triomas, because they are descended from three cells—two human and one mouse. Initially, a mouse myeloma line is fused with a human B-lymphocyte to obtain a non-antibody-producing xenogeneic hybrid cell, such as the SPAZ-4 cell line described by Oestberg, supra. The xenogeneic cell is then fused with an immunized human B-lymphocyte to obtain an antibody-producing trioma cell line. Triomas have been found to produce antibody more stably than ordinary hybridomas made from human cells.

The immunized B-lymphocytes are obtained from the blood, spleen, lymph nodes or bone marrow of a human donor. In vivo immunization of a living human with L-selectin is usually undesirable because of the risk of initiating a harmful response. Thus, B-lymphocytes are usually immunized in vitro with an L-selectin polypeptide, an antigenic fragment thereof or a cell bearing either of these. If antibodies against a specific antigen or epitope are desired, it is preferable to use that antigen or epitope thereof for in vitro immunization. B-lymphocytes are typically exposed to antigen for a period of 7–14 days in a media such as RPMI-1640 (see Engleman, supra) supplemented with 10% human plasma.

The immunized B-lymphocytes are fused to a xenogeneic hybrid cell such as SPAZ-4 by well known methods. For example, the cells are treated with 40–50% polyethylene glycol of MW 1000–4000, at about 37 degrees, for about 5–10 min. Cells are separated from the fusion mixture and propagated in media selective for the desired hybrids (e.g., HAT or AH). Clones secreting antibodies having the required binding specificity are identified by assaying the trioma culture medium for the ability to bind to L-selectin or a fragment thereof. Triomas producing human antibodies having the desired specificity are subcloned by the limiting dilution technique and grown in vitro in culture medium. The trioma cell lines obtained are then tested for the ability to bind L-selectin or a fragment thereof.

Although triomas are genetically stable they do not produce antibodies at very high levels. Expression levels can be increased by cloning antibody genes from the trioma into one or more expression vectors, and transforming the vector into a cell line such as the cell lines discussed supra for expression of recombinant or humanized immunoglobulins.

b. Transgenic Non-Human Mammals

Human antibodies against L-selectin can also be produced from non-human transgenic mammals having transgenes encoding at least a segment of the human immunoglobulin locus. Usually, the endogenous immunoglobulin locus of such transgenic mammals is functionally inactivated. Preferably, the segment of the human immunoglobulin locus includes unrearranged sequences of heavy and light chain components. Both inactivation of endogenous immunoglobulin genes and introduction of exogenous immunoglobulin genes can be achieved by targeted homologous recombination, or by introduction of YAC chromosomes. The transgenic mammals resulting from this process are capable of functionally rearranging the immunoglobulin component sequences, and expressing a repertoire of antibodies of various isotypes encoded by human immunoglobulin genes, without expressing endogenous immunoglobulin genes. The production and properties of mammals having these properties are described in detail by, e.g., Lonberg et al., WO93/12227 (1993); Kucherlapati, WO 91/10741 (1991) (each of which is incorporated by reference in its entirety for all purposes). Transgenic mice are particularly suitable. Anti-L-selectin antibodies are obtained by immunizing a transgenic nonhuman mammal, such as described by Lonberg or Kucherlapati, supra, with L-selectin or a fragment thereof. Monoclonal antibodies are prepared by, e.g., fusing B-cells from such mammals to suitable myeloma cell lines using conventional Kohler-Milstein technology.

c. Phage Display Methods

A further approach for obtaining human anti-L-selectin antibodies is to screen a DNA library from human B cells according to the general protocol outlined by Huse et al., *Science* 246:1275–1281 (1989). Antibodies binding to L-selectin or a fragment thereof are selected. Sequences encoding such antibodies (or a binding fragments) are then cloned and amplified. The protocol described by Huse is rendered more efficient in combination with phage-display technology. See, e.g., Dower et al., WO 91/17271 and McCafferty et al., WO 92/01047 (each of which is incorporated by reference in its entirety for all purposes). In these methods, libraries of phage are produced in which members display different antibodies on their outer surfaces. Antibodies are usually displayed as Fv or Fab fragments. Phage displaying antibodies with a desired specificity are selected by affinity enrichment to an L-selectin polypeptide or fragment thereof.

In a variation of the phage-display method, human antibodies having the binding specificity of a selected murine antibody can be produced. See Winter, WO 92/20791. In this method, either the heavy or light chain variable region of the selected murine antibody (e.g., mouse DREG-200) is used as a starting material. If, for example, a light chain variable region is selected as the starting material, a phage library is constructed in which members displays the same light chain variable region (i.e., the murine starting material) and a different heavy chain variable region. The heavy chain variable regions are obtained from a library of rearranged human heavy chain variable regions. A phage showing strong specific binding for L-selectin (e.g., at least $10^8$ and preferably at least $10^9$ $M^{-1}$) is selected. The human heavy chain variable region from this phage then serves as a starting material for constructing a further phage library. In this library, each phage displays the same heavy chain variable region (i.e., the region identified from the first display library) and a different light chain variable region. The light chain variable regions are obtained from a library of rearranged human variable light chain regions. Again, phage showing strong specific binding for L-selectin are selected. These phage display the variable regions of completely human anti-L-selectin antibodies. These antibodies usually have the same or similar epitope specificity as the murine starting material (e.g., mouse DREG-200).

Methods of Use

The antibodies of the present invention will typically find use in the treatment of disease conditions with an inflammatory component, especially those which are mediated by neutrophils or T cells. A preferred application is the therapeutic and prophylactic treatment of ischemia-reperfusion injury caused by myocardial infarction, cerebral ischemic event (e.g., stroke), renal, hepatic or splenal infarction, brain surgery, shock, cardiac surgery (e.g., coronary artery bypass), elective angioplasty, and the like. Other preferred applications are the treatment of sepsis, adult respiratory distress syndrome, and multiple organ failure. The antibodies will find use in treating injury due to trauma, burns, frostbite or damage to the spinal cord. They will also find use in treating autoimmune diseases including by way of example and not limitation, rheumatoid arthritis, systemic lupus erythematosus, multiple sclerosis, type I diabetes and uveitis, in treating inflammatory diseases of the skin such as psoriasis, and in treating meningitis and encephalitis. Other typical applications are the prevention and treatment of organ transplant rejection and graft-versus-host disease.

Any immunoglobulin of the present invention may also be used in combination with other antibodies, particularly humanized or human antibodies reactive with different adhesion molecules. For example, suitable immunoglobulins include those specific for CD11a, CD11b, CD18, E-selectin, P-selectin and ICAM-1. Other suitable antibodies are those specific for lymphokines, such as IL-1, IL-2 and IFN-γ, and their receptors.

The antibodies of the invention can also be used as separately administered compositions given in conjunction with chemotherapeutic agents. Typically, the agents may include non-steroidal anti-inflammatory drugs and corticosteroids, but numerous additional agents (e.g., cyclosporin) well-known to those skilled in the art of medicine may also be utilized. Indeed, the immunoglobins of the present invention will typically be used in combination with drugs currently used by those skilled in the art to treat particular diseases.

In some therapeutic methods, for example, anti-L-selectin antibodies are used in combination with thrombolytic agents. In previous methods, patients with acute myocardial infarction are often treated by opening the occluded coronary artery. Reopening of the obstructed coronary artery can be achieved by administration of thrombolytic agents which lyse the clot causing the obstruction, and which, thereby, restore coronary blood flow. Reperfusion of the vessel can also be achieved by acute percutaneous transluminal coronary angioplasty (PTCA) by means of balloon dilation of the obstructed and narrowed segment of the coronary artery. However, restoration of coronary blood flow leads to ischemia-reperfusion injury in prior methods.

In the present methods, ischemia-reperfusion injury is reduced or prevented by combination of a thrombolytic agent or of PTCA with humanized or human anti-L-selectin antibodies. Antibodies are usually administered prophylactically before, or at the same time as, administration of thrombolytic agents or initiation of PTCA. Further doses of antibody are then often administered during and after thrombolytic or angioplastic treatment. The interval between prophylactic administration of the antibodies and initiation of thrombolytic or angioplastic treatment is usually 5–30 mins, preferably 5–20 min, and most preferably 5–10 min. The antibodies are administered parentally, preferably by intravenous injection, in doses of 0.01–10 mg/kg body weight, preferably of 0.14–5 mg/kg and most preferably of 0.3–3 mg/kg. The antibodies can be given as an intravenous bolus injection, e.g., over 1–5 min, as repeated injections of smaller doses, or as an intravenous infusion. The bolus injection is especially useful for the prophylactic dose or in an emergency. Further doses of antibodies can be repeated (e.g., every 4–6 h) during and after thrombolytic or angioplastic treatment of acute myocardial infarction at the same proportions as described above to achieve optimal plasma levels of the antibody.

Thrombolytic agents are drugs having the capacity, directly or indirectly, to stimulate dissolution of thrombi in vivo. Thrombolytic agents include tissue plasminogen activator (see EP-B 0 093 619), activase, alteplase, duteplase, silteplase, streptokinase, anistreplase, urokinase, heparin, warfarin and coumarin. Additional thrombolytic agents include saruplase and vampire bat plasminogen activator. See Harris, *Protein Engineering* 6:449–458 (1987); PCT/EP 90/00194; U.S. Pat. No. 4,970,159). Thrombolytic agents are administered to a patient in an amount sufficient to partially disperse, or prevent the formation of, thrombi and their complications. An amount adequate to accomplish this is defined as a "therapeutically effective dose" or "efficacious dose." Amounts effective for this use will depend upon the severity of the condition, the general state of the patient, the route of administration and combination with other drugs. Often, therapeutically effective doses of thrombolytic agents and administration regimens for such agents are those approved by the FDA, for independent uses of thrombolytic agents, e.g., 100 mg of alteplase or 1.5 million IU of streptokinase.

A preferred pharmaceutical composition of the present invention comprises the use of the subject immunoglobulins in immunotoxins to kill L-selectin expressing cells. Immunotoxins are characterized by two components and are particularly useful for killing selected cells in vitro or in vivo. One component is a cytotoxic agent which is usually fatal to a cell when attached or absorbed. The second component, known as the "delivery vehicle," provides a means for delivering the toxic agent to a particular cell type, such as cells expressing a L-selectin epitope. The two components are commonly chemically bonded together by any of a variety of well-known chemical procedures. For example, when the cytotoxic agent is a protein and the second component is an intact immunoglobulin, the linkage may be by way of heterobifunctional cross-linkers, e.g., SPDP, carbodiimide, glutaraldehyde, or the like. Production of various immunotoxins is well-known with the art, and can be found, for example in "Monoclonal Antibody-Toxin Conjugates: Aiming the Magic Bullet," Thorpe et al., *Monoclonal Antibodies in Clinical Medicine,* Academic Press, pp. 168–190 (1982), which is incorporated herein by reference in its entirety for all purposes. The components may also be linked genetically (see Chaudhary et al., *Nature* 339:394 (1989), incorporated herein by reference in its entirety for all purposes).

A variety of cytotoxic agents are suitable for use in immunotoxins. Cytotoxic agents can include radionuclides, such as Iodine-131 or other isotopes of iodine, Yttrium-90, Rhenium-188, and Bismuth-212 or other alpha emitters; a number of chemotherapeutic drugs, such as vindesine, methotrexate, adriamycin, and cisplatin; and cytotoxic proteins such as ribosomal inhibiting proteins like pokeweed antiviral protein, Pseudomonas exotoxin A, ricin, diphtheria toxin, ricin A chain, etc., or an agent active at the cell surface, such as the phospholipase enzymes (e.g., phospholipase C). (See generally commonly assigned U.S. Ser. No. 07/290,968, "Chimeric Toxins," Olsnes and Phil, *Pharmac. There.,* 25:355–381 (1982), and *Monoclonal Antibodies for Cancer Detection and Therapy* (eds. Baldwin and Byers, Academic Press, 1985), pp. 159–179, 224–266, all of which are incorporated herein by reference in their entirety for all purposes.)

The delivery component of the immunotoxin will include the immunoglobulins of the present invention. Intact immunoglobulins or their binding fragments, such as Fab or Fv, are preferably used. Typically, the antibodies in the immunotoxins will be of the human IgM or IgG isotype, but other mammalian constant regions may be utilized as desired.

The antibodies and pharmaceutical compositions thereof of this invention are particularly useful for parenteral administration, i.e., subcutaneously, intramuscularly or intravenously. The antibodies of the invention may also be administered, typically for local application, by gavage or lavage, intraperitoneal injection, ophthalmic ointment, topical ointment, intracranial injection (typically into a brain ventricle), intrapericardiac injection, or intrabursal injection. The compositions for parenteral administration will commonly comprise a solution of the immunoglobulin or a cocktail thereof dissolved in an acceptable carrier, preferably an aqueous carrier. A variety of aqueous carriers can be used, e.g., water, buffered water, phosphate buffered saline (PBS), 0.4% saline, 0.3% glycine, human albumin solution and the like. These solutions are sterile and generally free of particulate matter. These compositions may be sterilized by conventional, well-known sterilization techniques. The compositions may contain pharmaceutically acceptable auxiliary substances as required to approximate physiological conditions such as pH adjusting and buffering agents, toxicity adjusting agents and the like, for example sodium acetate, sodium chloride, potassium chloride, calcium chloride and sodium lactate. The concentration of antibody in these formulations can vary widely, i.e., from less than about 0.005%, usually at least about 1% to as much as 15 or 20% by weight and will be selected primarily based on fluid volumes, viscosities, etc., in accordance with the particular mode of administration selected.

Thus, a typical pharmaceutical composition for injection could be made up to contain 1 ml sterile buffered water, and 1–70 mg of immunoglobulin. A typical composition for intravenous infusion could be made up to contain 250 ml of sterile Ringer's solution, and 150 mg of antibody. Actual methods for preparing parenterally administrable compositions will be known or apparent to those skilled in the art and are described in more detail in, for example, *Remington's Pharmaceutical Science* (15th ed., Mack Publishing Company, Easton, Pa., 1980), which is incorporated herein by reference in its entirety for all purposes. Compositions suitable for lavage or other routes will be selected according to the particular use intended. Some pharmaceutical compositions comprise both anti-L-selectin antibodies and thrombolytic agents.

The antibodies of this invention can be frozen or lyophilized for storage and reconstituted in a suitable carrier prior to use. This technique has been shown to be effective with conventional immune globulins and art-known lyophilization and reconstitution techniques can be employed. It will be appreciated by those skilled in the art that lyophilization and reconstitution can lead to varying degrees of antibody activity loss (e.g., with conventional immune globulins, IgM antibodies tend to have greater activity loss than IgG antibodies) and that use levels may have to be adjusted to compensate.

The compositions containing the present antibodies or a cocktail thereof can be administered for prophylactic and/or therapeutic treatments. In therapeutic applications, compositions are administered to a patient already suffering from an inflammatory disease, in an amount sufficient to cure or at least partially arrest the disease and its complications. An amount adequate to accomplish this is defined as a "therapeutically effective dose." Amounts effective for this use will depend upon the severity of the disease and the general state of the patient's own immune system, but generally range from about 1 to about 200 mg of antibody per dose, with dosages of from 5 to 70 mg per patient being more commonly used. Dosing schedules will vary with the disease state and status of the patient, and will typically range from a single bolus dosage or continuous infusion to multiple administrations per day (e.g., every 4–6 hours), or as indicated by the treating physician and the patient's condition. It must be kept in mind that the materials of this invention may generally be employed in serious disease states, that is life-threatening or potentially life-threatening situations. In such cases, in view of the minimization of extraneous substances and the lower probability of "foreign substance" rejections which are achieved by the immunoglobulins of this invention, it is possible and may be felt desirable by the treating physician to administer substantial excesses of these antibodies.

In prophylactic applications, compositions containing the present antibodies or a cocktail thereof are administered to a patient not already suffering from a particular disease to enhance the patient's resistance. Such an amount is defined to be a "prophylactically effective dose." In this use, the precise amounts again depend upon the patient's state of health and general level of immunity, but generally range from 1 to 70 mg per dose. Preferred prophylactic uses are for the prevention of adult respiratory distress syndrome in patients already suffering from sepsis or trauma; prevention of organ transplant rejection; and prevention of reperfusion injury in patients suffering from ischemia. In seriously ill patients, dosages of about 50 to 150 mg of humanized or human immunoglobulin per administration are frequently used, and larger dosages may be indicated.

Single or multiple administrations of the compositions can be carried out with dose levels and pattern being selected by the treating physician. In any event, the pharmaceutical formulations should provide a quantity of the antibody(ies) of this invention sufficient to effectively treat the patient.

Antibodies of the present invention can further find a wide variety of utilities in vitro. By way of example, the antibodies can be utilized for detection of L-selectin antigens, for isolating specific leukocytes, or the like. For example, but not for limitation, a humanized DREG-200 immunoglobulin can be immobilized and contacted with blood extravasated from a patient to remove blood cells bearing L-selectin antigens, and the remaining blood, depleted of L-selectin-bearing cells, may be reintroduced into the patient. Any residual humanized antibody present in the depleted blood reintroduced into the patient (e.g., as a consequence of detachment from the immobilization support) would have reduced or negligible antigenicity as compared to a murine antibody.

For diagnostic purposes, the antibodies may either be labeled or unlabeled. Unlabeled antibodies can be used in combination with other labeled antibodies (second antibodies) that are reactive with the humanized or human antibody, such as antibodies specific for human immunoglobulin constant regions. Alternatively, the antibodies can be directly labeled. A wide variety of labels may be employed, such as radionuclides, fluors, enzymes, enzyme substrates, enzyme co-factors, enzyme inhibitors, ligands (particularly haptens), etc. Numerous types of immunoassays are available and are well known to those skilled in the art.

The following examples are offered by way of illustration, not by limitation. It will be understood that although the examples pertain to the mouse DREG-200 or DREG-55 antibody, humanized antibodies with high binding affinity for L-selectin can also be produced using CDRs from other monoclonal antibodies that bind to an epitope of L-selectin.

EXAMPLES

Example 1
Cloning of Heavy Chain and Light Chain cDNA cDNAs for the heavy chain and light chain variable domain genes of mouse DREG-200 were cloned using anchored polymerase chain reactions as described (see Co et al., *J. Immunol.* 148:1149 (1992) and commonly assigned U.S. Ser. No. 07/634,278), using 3' primers that hybridized to the constant regions and contained HindIII sites, and 5' primers that hybridized to the dG tails and contained EcoRI sites. The PCR amplified fragments were digested with EcoRI and HindIII and cloned into the pUC18 vector for sequencing. For mouse DREG-200, at least two gamma-1 specific and two kappa specific clones were sequenced. The gamma-1 clones and the kappa clones are respectively identical in sequence. The cDNA variable domain sequences and the deduced amino acid sequences are shown in FIG. 1.

Example 2
Computer Modeling of Humanized Antibodies

In order to retain high binding affinity in the humanized antibodies, the general procedures of Queen et al. were followed (see Queen et al., *Proc. Natl. Acad. Sci. USA* 86:10029 (1989) and WO 90/07861, which are incorporated herein by reference in their entirety for all purposes). The more homologous an acceptor human antibody is to the original murine donor antibody, the less likely will combining the murine CDRs with the human framework be to introduce distortions into the CDRs that could reduce affinity. Homology (that is, percent sequence identity) of at least 65% between the humanized immunoglobulin heavy chain variable region framework and the donor immunoglobulin heavy chain variable region framework is preferred. Normally the heavy chain and light chain from the same human antibody are chosen to provide the framework sequences, so as to reduce the possibility of incompatibility in the assembling of the two chains. Based on sequence homology search against the NBRF protein sequence database (performed with the MicroGenie Sequence Analysis Software (Beckman)), the antibody Eu was chosen to provide the framework sequences for humanization of mouse DREG-200.

The computer program ENCAD (Levitt, *J. Mol. Biol.* 168:595 (1983)), which is incorporated herein by reference in its entirety for all purposes) was used to construct a model of the mouse DREG-200 variable region. The model was used to determine the amino acids in the mouse DREG-200 framework that were close enough to the CDRs to potentially interact with them (category 4 below). To design the humanized light and heavy chain DREG-200 variable regions, at each position the amino acid was chosen to be the same as in the Eu antibody, unless that position fell in one or more of five categories:

(1) The position fell within a CDR,
(2) The Eu amino acid was unusual for human antibodies at that position, whereas the mouse DREG-200 amino acid was typical for human antibodies at that position,
(3) The position was immediately adjacent to a CDR,
(4) The model described above suggested that the amino acid may be physically close to the antigen binding region (CDRs).

For positions in these categories, the amino acid from the mouse DREG-200 antibody was used.

In addition, a position was in the fifth category if
(5) The Eu amino acid was highly unusual for human antibodies at that position, and the mouse DREG-200 amino acid was different but also unusual. Then an amino acid typical for human antibodies at that position was used.

The amino acids in each category are shown in Table 1. Some amino acids may be in more than one category. The final sequences of the humanized DREG-200 light and heavy chain variable domains are shown in FIG. 2, compared with the murine DREG-200 sequences.

TABLE 1

| Category | Light Chain | Heavy Chain |
|---|---|---|
| 1 | 24–40, 56–62, 95–103 | 31–35, 50–66, 99–110 |
| 2 | 87 | 93, 95, 98, 111, 112, 115 |
| 3 | — | 30, 98, 111 |
| 4 | 54, 66, 76, 93 | 27, 30, 48, 72 |
| 5 | — | 113 |

For the construction of genes for the humanized antibodies, nucleotide sequences were selected that encode the protein sequences of the humanized heavy and light chains, including signal peptides, generally utilizing codons found in the mouse sequence. Several degenerate codons were changed to create restriction sites or to remove undesirable ones. The nucleotide sequences of the genes also included splice donor signals and an XbaI site at each end. The nucleotide sequences and encoded humanized light and heavy chain variable domains are shown in FIG. 3. Each gene was constructed from four overlapping synthetic oligonucleotides, as described (see Co et al., *J. Immunol.* 148:1149 (1992), and commonly assigned U.S. Ser. No. 07/634,278, which are incorporated herein by reference in their entirety for all purposes.) The heavy and light chain variable region genes were then respectively ligated into the XbaI sites of the pVg1-dhfr or pVk expression vectors (see commonly assigned U.S. Ser. No. 07/634,278) in the appropriate orientations to produce the complete heavy and light chain genes. Reactions were carried out under conditions well-known in the art (Maniatis et al., supra)

The heavy chain and light chain plasmids were transfected into Sp2/0 mouse myeloma cells by electroporation and cells were selected for gpt expression. Clones were screened by assaying human antibody production in the culture supernatant by ELISA, and antibody was purified from the best-producing clones. Humanized DREG-200 IgG1 antibody was then purified by passing tissue culture supernatant over a column of staphylococcal protein A-SEPHAROSE™ matrix CL-4B (Pharmacia). The bound antibody was eluted with 0.2 M Glycine-HCl, pH3.0 and neutralized with 1 M Tris pH 8.0. The buffer was exchanged into PBS by passing over a PD10 column (Pharmacia), or by dialysis. To obtain cells producing higher levels of antibody, the transfected clones may be cultured in increasing concentrations of methotrexate.

To produce a humanized DREG-200 antibody of the IgG4 isotype, another vector pVg4-dhfr was first constructed. To do so, the XbaI-BamHI fragment of pVg1-dhfr containing the γ1 constant region was replaced with an approximately 2000 bp fragment of the human γ4 constant region gene (Ellison and Hood, *Proc. Natl. Acad. Sci. USA* 79:1984 (1982)) that extended from the HindIII site preceding the $C_H1$ exon of the γ4 gene to 270 bp after the NsiI site following the $C_H4$ exon of the gene, using methods well-known to those skilled in the art, including polymerase chain reaction. The humanized DREG-200 heavy chain variable region gene was then cloned into the XbaI site of pVg4-dhfr. This heavy chain plasmid was then transfected together with the above light chain plasmid into Sp2/0 cells, clones selected, and humanized DREG-200 IgG4 antibody purified as described above for the IgG1 antibody.

Example 3
Properties of Humanized Antibodies

The affinity of the humanized DREG-200 antibodies for L-selectin were determined by competition with the radio-iodinated mouse DREG-200 antibody (FIG. 4). The binding affinities were calculated according to the methods of Berzofsky (J. A. Berzofsky and I. J. Berkower, in *Fundamental Immunology* (ed. W. E. Paul), Raven Press (New York), 595 (1984), which is incorporated herein by reference in its entirety for all purposes). The humanized DREG-200 antibodies had an affinity within about 2-fold of the mouse DREG-200 antibody. A similar result will be found when the affinity for L-selectin on human neutrophils is measured.

Figure 5A:
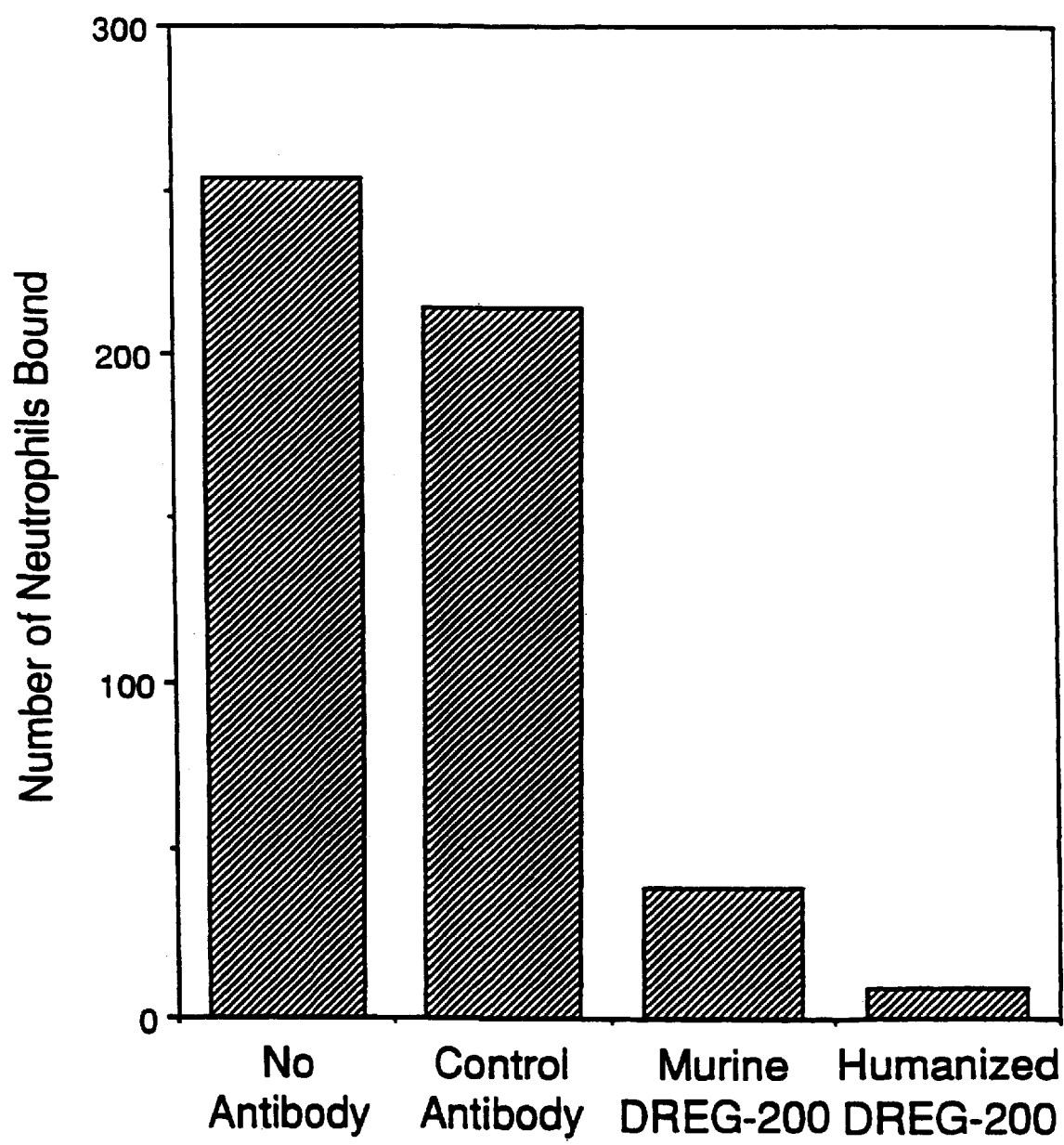
FIG. 5A. Binding of human neutrophils to IL-1 stimulated human umbilical cord endothelial cells (HUVEC). The neutrophils were first treated with irrelevant control antibody, mouse DREG-200 antibody, or humanized IgG1 DREG-200 antibody, or left untreated, as indicated.

The ability of the mouse and humanized DREG-200 antibodies to block the adhesion of human neutrophils to endothelial cells was determined using a modification of the assay method of Hallmann et al., *Biochem. Biophys. Res. Comm.* 174:236 (1991). Specifically, human umbilical cord endothelial cells (HUVEC; from Clonetics, San Diego) were grown to confluence in EGM medium (Clonetics) in Lab-Tek 8-chamber slides (Nunc, Naperville, Ill.). The HUVEC cells were stimulated with 20 ng/ml IL-1β (R&D Systems, Minneapolis, Minn.) for 4 hr before use. Neutrophils were isolated by density gradient centrifugation from buffy coats that had been cleared of erythrocytes by dextran sedimentation, and then adjusted to $10^7$ per ml. The neutrophils (100 μl) were pre-incubated for 20 minutes on ice with varying concentrations of antibody (in 100 μl RPMI). The HUVEC slides were washed free of IL-1β and placed on a rotary shaker (100 rpm) at 4° C. The untreated or antibody treated neutrophils were added to the chambers, and the slide was incubated at 4° C. on the shaker for 30 min. The slides were then washed by dipping ten times into a beaker of RPMI, fixed in 1% glutaraldehyde in RPMI, and allowed to air dry. Neutrophil adherence was quantified by counting the neutrophils attached to a defined area of the endothelial cell monolayer with a microscope. As shown in FIG. 5A, the humanized IgG1 and mouse DREG-200 antibodies both effectively blocked the binding of neutrophils to the HUVEC, while an irrelevant control antibody did not. The humanized DREG-200 IgG4 antibody will similarly block binding of neutrophils to endothelial cells.

Example 4
Effect of hu DREG-200 on Myocardial Injury Following Reperfusion

The effect of humanized DREG-200 of the IgG4 isotype (hu DREG-200) on the degree of actual salvage of myocardial ischemic tissue following reperfusion was investigated. Adult male cats (2.8–4.2 kg) were anesthetized with sodium pentobarbital (30 mg/kg, i.v.). An intratracheal cannula was inserted through a midline incision, and the cats were placed on intermittent positive-pressure ventilation (Harvard small animal respirator, Dover, Mass.). A polyethylene catheter was inserted into the right external jugular vein for additional pentobarbital infusion in order to maintain a surgical plane of anesthesia and for administration of antibodies. Another polyethylene catheter was inserted through the left femoral artery and positioned in the abdominal aorta for the measurement of mean arterial blood pressure (NABP) via a pressure transducer (Cobe Instruments, Lakewood, Colo.). After a midsternal thoracotomy, the anterior pericardium was incised, and a 3-0 silk suture was placed around the left anterior descending (LAD) coronary artery 8 to 10 mm from its origin. A high-fidelity catheter tip pressure transducer (Model MPC 500, with transducer control unit—Model TCB 500, Millar Instruments Inc., Houston, Tex.) was introduced into the left ventricle through the apical dimple. The catheter was positioned via observation of the LV pressure and dP/dt wave forms and then secured in place by a silk suture. Standard lead II of the scalar electrocardiogram (ECG) was used to determine heart rate (HR) and ST-segment elevation. ST-segment elevations were determined by analysis of the ECG recording at 50 mm/sec every 20 min. The ECG, MABP, LVP and dP/dt were continuously monitored on a Hewlett-Packard 78304 A unit (Hewlett-Packard, Palo Alto, Calif.) and recorded on a Gould oscillographic recorder (Gould Inc., Cleveland, Ohio) every 20 min. The pressure-rate index (PRI), an approximation of myocardial oxygen demand, was calculated as the product of MABP and HR divided by 1000.

After completing all surgical procedures, the cats were allowed to stabilize for 30 minutes, at which time baseline readings of ECG, MABP, LVP and dP/dt were recorded. Myocardial ischemia (MI) was induced by tightening the initially placed reversible ligature around the LAD so that the vessel was completely occluded. This was designated as time point zero. 2 mg/kg body weight of hu DREG-200 (IgG4 isotype) or a control MAb hu ABL-364 (i.e., isotype-matched humanized control IgG4 MAb) was given intravenously as a bolus 80 min after coronary occlusion (i.e., 10 min prior to reperfusion, R). 10 min later (i.e., after a total of 90 min ischemia, I) the LAD ligature was untied and the ischemic myocardium was reperfused for 4.5 h.

The cats were randomly divided into three major groups. Six sham MI+R cats received hu DREG-200 (2 mg/kg), six MI+R cats received the control MAb hu ABL-364 (2 mg/kg), and six MI+R cats received hu DREG-200 (2 mg/kg). Sham MI+R cats were subjected to the same surgical procedures as MI+R cats except that the LAD coronary artery was not occluded.

At the end of the 4.5 h reperfusion period, the ligature around the LAD was again tightened. 20 ml of 0.5% Evans blue was rapidly injected into the left ventricle to stain the area of myocardium which was perfused by the patent coronary arteries. The area-at-risk was determined by negative staining. Immediately following this injection, the heart was rapidly excised and placed in warmed, oxygenated K-H solution. The left circumflex (LCX) and the LAD coronary arteries were isolated and removed for subsequent study of coronary ring vasoactivity and PMN adherence. The right ventricle, great vessels, and fat tissue were carefully removed, and the left ventricle was sliced parallel to the atrioventricular groove in 3 mm thick sections. The unstained portion of the myocardium (i.e., the total area-at-risk or ischemic area) was separated from the Evans blue stained portion of the myocardium (i.e., the area-not-at-risk or nonischemic area). The area-at-risk was sectioned into small cubes and incubated in 0.1% nitroblue tetrazolium in phosphate solution at pH 7.4 and 37° C. for 15 min. The tetrazolium dye forms a blue formazan complex in the presence of myocardial cells containing active dehydrogenases and their cofactors. The irreversibly injured or necrotic portion of the myocardium-at-risk, which did not stain, was separated from the stained portion of the myocardium (i.e., the ischemic but non-necrotic area). The three portions of the myocardium (i.e., non-ischemic, ischemic non-necrotic, and ischemic necrotic tissue) were subsequently weighed. Results were expressed as necrotic cardiac tissue area as a percentage of either the area-at-risk or of total left ventricular mass.

Figure 5B:
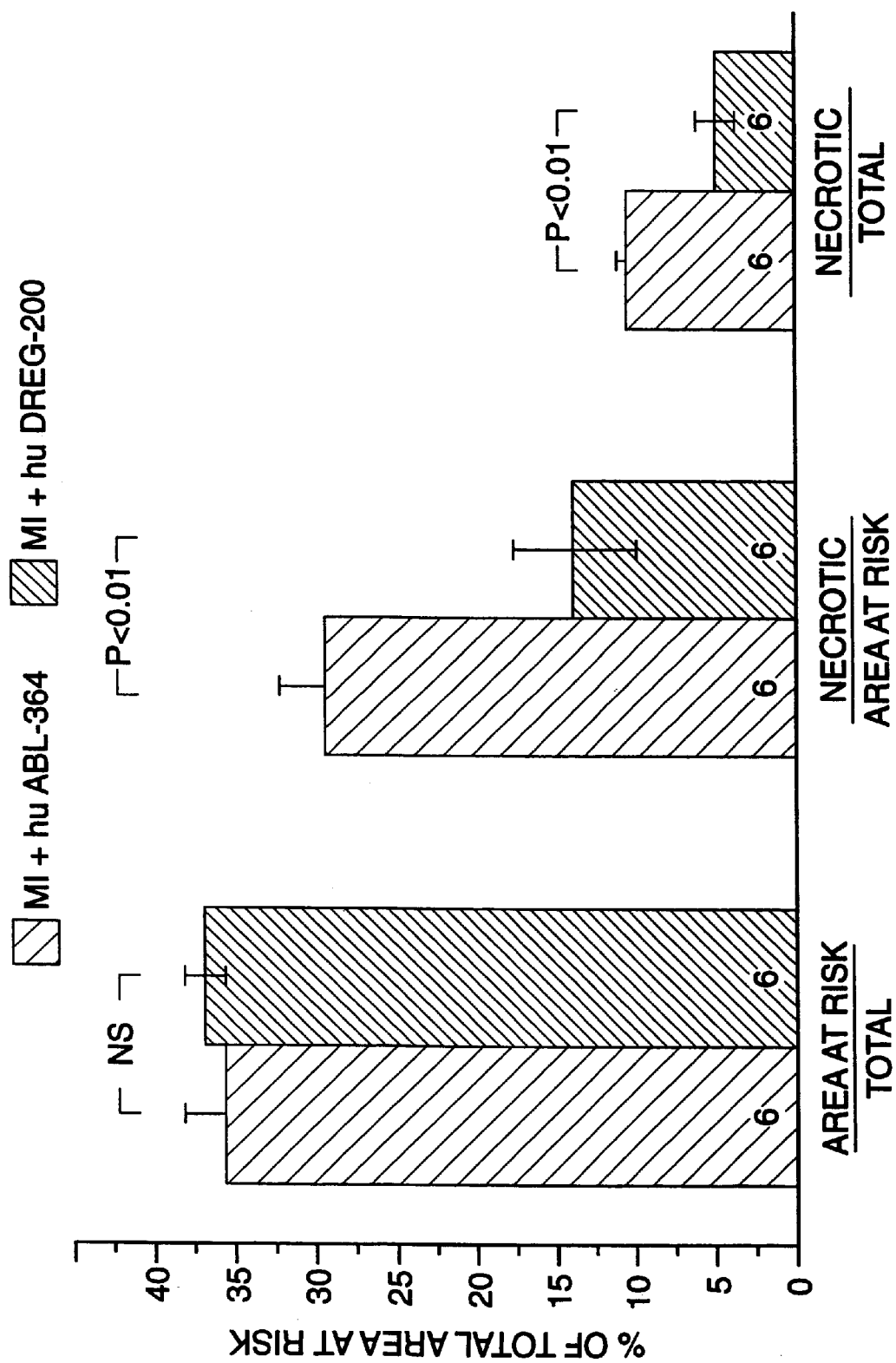
FIG. 5B. Protection of ischemic-reperfused heart tissue by humanized DREG-200. The Figure shows for cats treated with humanized DREG-200 or control antibody, from left to right: area at risk/total ventricular area; necrotic tissue area/area at risk; and necrotic tissue area/total left ventricle area. Brackets represent+/−SEM for six cats; heights of bars are means.

According to both of these criteria, cardiac tissue damage was significantly attenuated ($p<0.001$) in cats treated with hu DREG-200. Whereas about 30% of the jeopardized myocardium developed into necrotic tissue in the group treated with the control antibody, the amount of necrotic tissue was less than 15% ($p<0.01$) in the hu DREG-200 treated group, a decrease of 50–60%. See FIG. 5B. There was no significant difference in the wet weights of the areas-at-risk expressed as a percentage of total left ventricle between the two ischemic groups, indicating that a comparable area of myocardial ischemia occurred in both groups. Therefore, hu DREG-200 significantly protects against reperfusion injury.

The remarkable preservation of ischemic tissue by hu DREG-200 is further illustrated from measurements of plasma creatine kinase activity, a biochemical marker of myocardial injury. Arterial blood samples (2 ml) were drawn immediately before ligation and hourly thereafter. The blood was collected in polyethylene tubes containing 200 IU of heparin sodium. Samples were centrifuged at 2000× g and 4° C. for 20 min and the plasma was decanted for biochemical analysis. Plasma protein concentration was assayed using the biuret method of Gornall et al., *J. Biol. Chem.* 177:751–766 (1949). Plasma creatine kinase (CK) activity was measured using the method of Rosalki, *J. Lab. Clin Med.* 69:696–705 (1967), and expressed as IU/$\mu$g protein.

In sham MI/R cats receiving hu DREG-200, the plasma CK activity increased slightly throughout the 6 hour observation period reaching a final value of 3.8±0.9 IU/$\mu$g protein. In the two ischemic groups, plasma CK activity increased slightly during the period of myocardial ischemia. In cats receiving hu ABL-364, CK activity in circulating blood increased markedly within the first 30 min follow reperfusion and further increased during the remaining four hours of reperfusion. By contrast, ischemic cats treated with hu DREG-200 developed significantly lower plasma CK activities compared with ischemic cats receiving the hu ABL-364 ($p<0.05$). The effect was sustained over the entire reperfusion period, further evidencing the substantial protection conferred by hu DREG-200 against myocardial reperfusion injury.

Example 5

Effect of hu DREG-200 on Cardiac Function

The effect of hu DREG-200 (IgG4 isotype) on cardiac function was determined by measurement of left ventricular pressure (LVP), and the first derivative of LVP, dP/dt max, an index of myocardial contractility. Data were obtained from a catheter tip manometer inserted in the left ventricular cavity. The three groups of cats discussed in the previous example all showed comparable initial values for these cardiac variables. In the sham MI group there were no significant changes in dP/dt max over the entire six hour experimental period. However, in both MI/R groups, dP/dt max decreased upon occlusion of the LAD to about 65%. In cats given hu ABL-364, contractility did not significantly recover. However, in hu DREG-200 treated MI-R cats, dP/dt max recovered to control values three hours following reperfusion. Hence, after 4.5 hours of reperfusion, dP/dt max was significantly lower in hu ABL-364 treated cats than in hu DREG-200 treated cats ($p<0.01$). These results indicate that hu DREG-200 not only reduced myocardial necrosis following reperfusion of the ischemic myocardium, but this myocardial salvage was also translated into an improvement in mechanical performance of the heart.

Example 6
Cloning of mouse DREG-55 heavy chain and light chain cDNA cDNAs for the heavy chain and light chain variable domain genes of mouse DREG-55 were cloned using anchored polymerase chain reactions as described (see Co et al., *J. Immunol.* 148, 1149 (1992) and commonly assigned U.S. Ser. No. 07/634,278), using 3' primers that hybridized to the constant regions and contained HindIII sites, and 5' primers that hybridized to the dG tails and contained EcoRI sites. The PCR amplified fragments were digested with EcoRI and HindIII and cloned into the pUC18 or pUC19 vectors for sequencing. For mouse DREG-55, at least two gamma-i specific and two kappa specific clones were sequenced. The gamma-i clones and the kappa clones are respectively identical in sequence. The variable domain cDNA sequences and the deduced amino acid sequences are shown in FIG. 6.

Computer modeling of DREG-55 variable region

In order to retain high binding affinity in the humanized antibody, the general procedures of Queen at. al were followed (see, Queen et al., Proc. Natl. Acad. Sci. USA 86, 10029 (1989) and WO 90/07861, which are incorporated herein by reference). The choice of framework residues can be critical in retaining high binding affinity. In principal, a framework sequence from any human antibody may serve as the template for CDR grafting. However, it has been demonstrated that straight CDR replacement often leads to significant loss of binding affinity to the antigen (Glaser et al., J. Immunol. 149, 2606 (1992); Tempest et al., Biotechnology 9, 266 (1992); Shalaby et al., J. Exp. Med. 174, 217 (1992)). The more homologous a human antibody is to the original murine antibody, the less likely will combining the murine CDRs with the human framework be to introduce distortions into the CDRs that could reduce affinity. Often, the heavy chain and light chain from the same human antibody are chosen to provide the framework sequences, so as to reduce the possibility of incompatibility in the assembly of the two chains. Based on sequence homology search against an antibody sequence database, the variable regions of light chain subgroup I and heavy chain subgroup III show good homology to the mouse DREG-55 antibody and are preferred to serve as acceptor sequences for the humanized DREG-55 antibody. In particular, the human antibody Gal provides high framework homology with DREG-55 and was chosen to provide the framework sequences for humanization of DREG-55.

The computer program ENCAD (M. Levitt, J. Mol. Biol. 168, 595 (1983), which is incorporated herein by reference) was used to construct a molecular model of the mouse DREG-55 variable domain. The model was used to determine the amino acids in the DREG-55 framework that are close enough to the CDRs to potentially interact with them. To design the humanized light and heavy chain DREG-55 variable regions, the CDRs (according to Kabat) from the mouse DREG-55 were grafted into the framework sequences of the Gal antibody. At the framework positions where the potential interactions with the CDRs were considered to be important from the model, the amino acids from the mouse DREG-55 were chosen to replace the residues in the Gal sequence at residues 50, 62 and 74 in the light chain. The heavy chain did not require any analogous substitutions. Moreover, at some framework positions where the amino acid was highly unusual for human antibodies at that position, an amino acid representing a consensus of the human antibody subgroup was substituted in place of the Gal framework residue. Examples are residues 22 and 71 in the light chain and residues 10, 16, 77, 87, 92 and 116 in the heavy chain.

The final sequence for the humanized DREG-55 antibody (HuDREG-55) heavy and light chain is shown in FIG. 7. However, many of the potential CDR interacting residues are amenable to substitutions of other amino acids which can still allow the antibody to retain substantial affinity to the antigen. The following table lists a number of positions in the framework where alternatives are possible:

TABLE 2

| Position | HuDREG-55 | Alternatives |
|----------|-----------|--------------|
| LC-3     | Q         | V            |
| LC-4     | M         | L            |
| LC-50    | L         | E            |
| LC-62    | I         | V            |
| LC-64    | S         | A            |
| LC-74    | D         | E            |
| HC-83    | N         | S            |

Likewise, many of the non-CDR-interacting framework residues in the humanized DREG-55 heavy and light chains are also amenable to substitutions with amino acids from either the original Gal antibody, or from the corresponding position of other human antibodies, or from the mouse DREG-55 or other mouse antibodies, and which still allow the antibody to retain substantial affinity to the antigen without causing immunogenicity. The following table lists a number of positions in the framework where alternatives can be considered:

TABLE 3

| Position | HuDREG-55 | Alternatives |
|----------|-----------|--------------|
| LC-22    | T         | S, I         |
| LC-71    | S         | A            |
| HC-10    | G         | D            |
| HC-16    | G         | R            |
| HC-49    | A         | S            |
| HC-74    | A         | S            |
| HC-77    | T         | S, I         |
| HC-87    | A         | V, S         |
| HC-92    | V         | L, M         |
| HC-116   | S         | T            |

Construction of humanized DREG-55

For the construction of variable region genes for the humanized DREG-55 antibody, nucleotide sequences were selected that encode the protein sequences of the humanized heavy and light chains, including the signal peptide, generally utilizing codons found in the mouse sequence. Several degenerate codons were changed to create restriction sites or to remove undesirable ones. The nucleotide sequences of the genes also included splice donor signals and an XbaI site at each end. The nucleotide sequences and encoded humanized light and heavy chain variable domains are shown in FIG. 7.

To construct the complete synthetic $V_L$ segment, 4 long oligonucleotides (115–123 nucleotides) overlapping on alternating DNA strands were synthesized (Applied Biosystems Model 380B Oligonucleotide Synthesizer). The appropriate oligos also contained XbaI or HindIII sites needed for cloning. The appropriate pairs of oligos were hybridized together, extended with AmpliTaq to make the DNA double-stranded, cut with XbaI and HindIII, and cloned between the XbaI and HindIII sites of the vector pUC19. These two "half-segments" were verified to have the correct sequences by dideoxy sequencing. The two half-segments were then excised from pUC19 with XbaI and HindIII and cloned into the XbaI site of pVk in a three-way ligation. The correct orientation and sequence of the complete variable region synthetic segment in pVk was then verified by sequencing again.

To construct the complete synthetic $V_H$ segment, 6 long oligonucleotides (64–121 nucleotides) overlapping on alternating DNA strands were synthesized to generate two half-segments. The first segment was constructed by hybridizing two long oligos, extended with AmpliTaq and cloned into the pUC19 vector for verification of segment sequence. The second segment was constructed by hybridizing four overlapping oligos, extended with Klenow polymerase and cloned into pUC19 for verification of segment sequence. The two half-segments were then excised from pUC19 with XbaI and XhoI and cloned into the XbaI site of pVg4 in a three-way ligation. The correct orientation and sequence of the complete variable region synthetic segment in pVg4 was then verified by sequencing again. All manipulations were performed by standard methods.

The pVk vector for light chain expression and the pVg1 vector for heavy chain expression have been previously described (see Co et al., J. Immunol. 148, 1149 (1992)). To produce a humanized DREG-55 antibody of the IgG4 isotype, the heavy chain expression vector pVg4 has been constructed. To do so, the XbaI-BamHI fragment of pVg1 containing the gamma1 constant region was replaced with an approximately 2000 bp fragment of the human gamma4 constant region gene (Ellison and Hood, Proc. Natl. Acad. Sci USA 79, 1984 (1982)) that extended from the HindIII side preceding the CH1 exon of the gamma4 gene to 270 bp after the NsiI site following the CH4 exon of the gene, using methods well-known to those skilled in the art.

The heavy chain and light chain plasmids were transfected into a mouse myeloma cell line Sp2/0-Ag14 (ATCC CRL 1581). Transfection was by electroporation using a Gene Pulser apparatus (Bio-Rad) at 360 V and 25 uFD capacitance according to the manufacturer's instructions. Before transfection, the light chain- and heavy chain-containing plasmids were linearized using BamHI, extracted with phenol-chloroform, and ethanol-precipitated. All transfections were done using 20–30 μg plasmid DNA and about $10^7$ cells in PBS. The cells from each transfection were plated into 2 96-well tissue culture plates. After 48 hr, selective medium was applied.

Cells were selected in DMEM+10% FBS+HT media supplement (Sigma)+1 μg/ml mycophenolic acid for gpt expression. Antibody-producing clones were screened by assaying human antibody production in the culture supernatant by ELISA. Antibody from the best-producing clones were purified by passing tissue culture supernatant over a column of staphylococcal protein A-SEPHAROSE™ matrix CL-4B (Pharmacia). The bound antibodies were eluted with 0.2 M glycine-HCl, pH 3.0, and neutralized with 1 M Tris-HCl, pH 8.0. The buffer was exchanged into phosphate buffered saline (PBS) by passing over a PD10 column (Pharmacia), or by dialysis. To obtain cells producing higher levels of antibody, the transfected clones can be cultured in increasing concentrations of methotrexate.

Properties of humanized DREG-55

Figure 8:
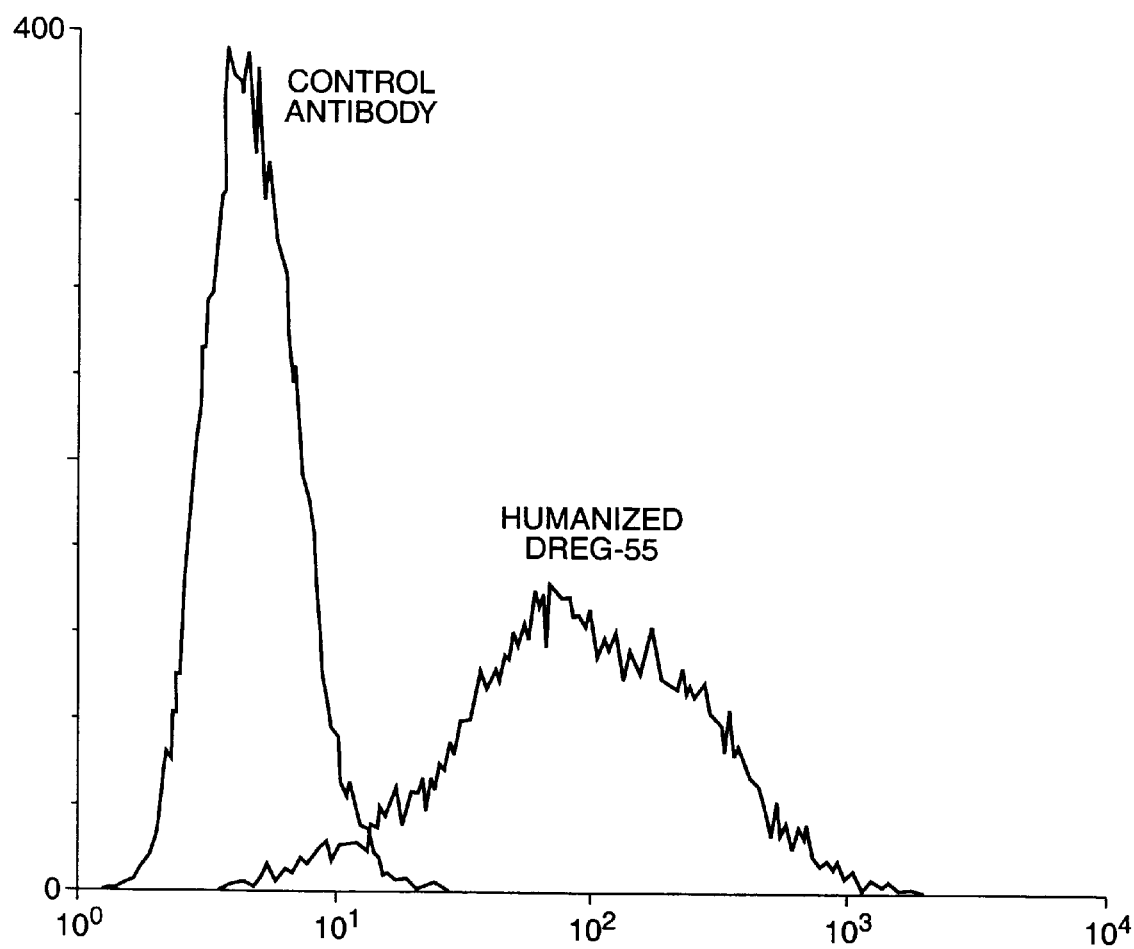
FIG. 8: Binding of humanized DREG-55 to L1-2$^{L-selectin}$ transfectants compared to binding of control antibody as analyzed by flow cytometry. Fluorescence intensity is indicated on the x-axis.

To show that humanized DREG-55 specifically binds to L-selectin, L1-2$^{L-selectin}$ transfectants, which were obtained by transfecting the L-selectin genes into the host L1-2 cell line, were incubated with humanized DREG-55 or control antibody for 1 hour. After washing, cells were incubated in a 1:250 dilution of FITC-conjugated goat anti-human Ig, washed, then analyzed for fluorescence by flow cytometry (FACS). Humanized DREG-55 reacts with the L1-2L-selectin transfectants, indicating the humanization process did not result in loss of binding specificity to L-selectin (FIG. 8).

Figure 9:
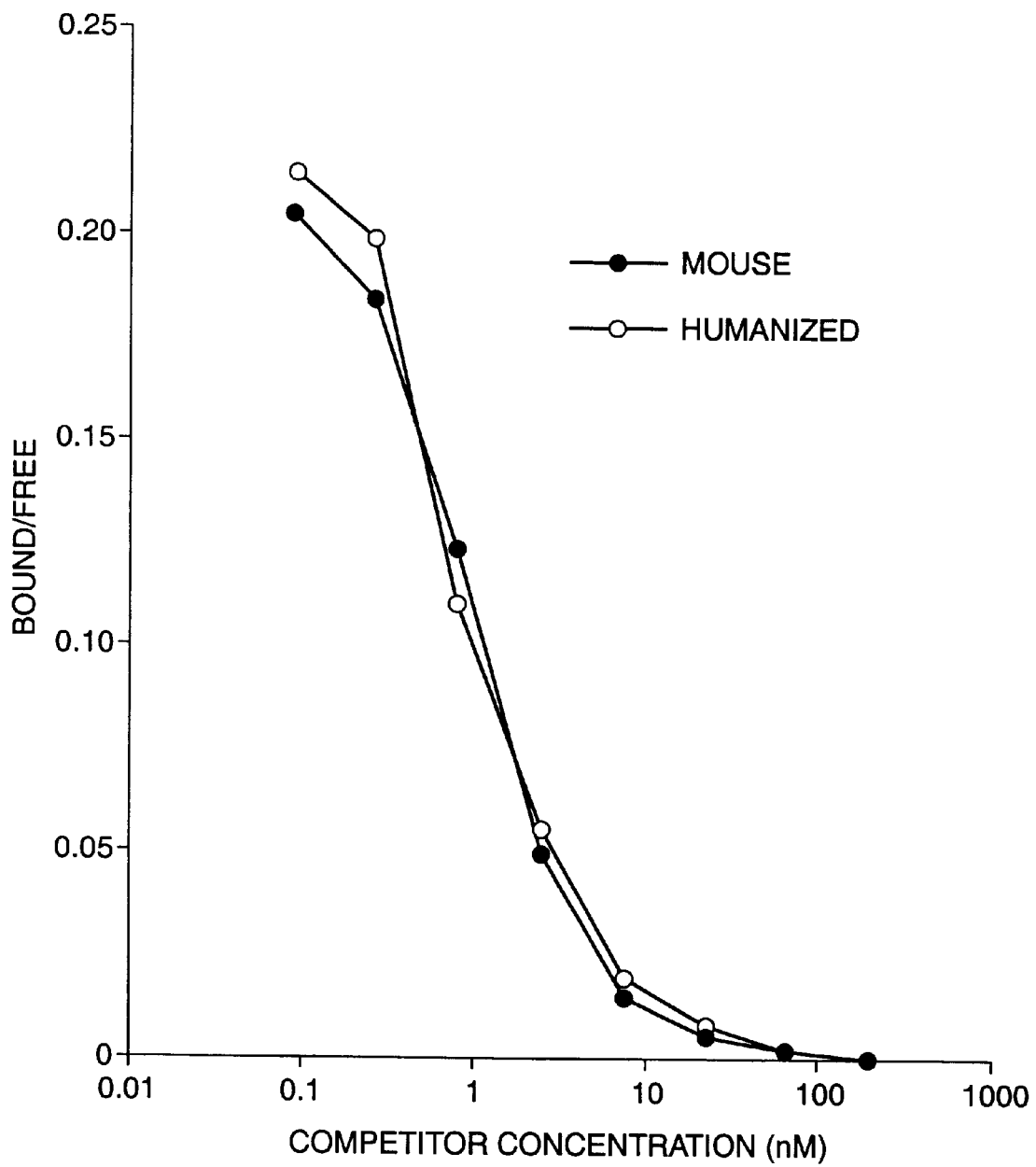
FIG. 9: Competitive binding of mouse and humanized DREG-55 antibodies to CHO$^{L-selectin}$ cells expressing L-selectin. Increasing concentrations of cold competitor antibody were incubated with the cells in the presence of radiolabeled tracer humanized DREG-55 antibody, and the ratio of bound/free radioactivity was determined.

The affinity of the humanized DREG-55 antibody for L-selectin was determined by competition with the radio-iodinated humanized DREG-55 antibody (FIG. 9). Purified humanized DREG-55 antibody was labeled with Na$^{125}$I (Amersham, Arlington Heights, Ill.) using lactoperoxidase to 4 mCi/mg of protein (Marchalonis, Biochem. J. 113, 299 (1969)). CHO$^{L-selectin}$ cells, which were obtained by transfecting the L-selectin genes into the host CHO cells, were used as a source for L-selectin. Increasing amounts of competitor antibody (mouse DREG-55 or humanized DREG-55) were added to 2 ng of radiolabeled tracer humanized DREG-55 antibody and incubated with 5×10$^5$ CHO$^{L-selectin}$ cells in 0.2 ml of binding buffer (PBS with 2% fetal calf serum, 0.1% sodium azide) for 2 hr at 4° C. with constant shaking. Cells were then washed and centrifuged, and their radioactivities measured. The ratio of bound and free tracer antibody were calculated. The binding affinities were calculated according to the methods of Berzofsky and Berkower (J. A. Berzofsky and I. J. Berkower, in Fundamental Immunology (ed. W. E. Paul), Raven Press (New York), p. 595 (1984), which is incorporated herein by reference). The humanized DREG-55 had an affinity of 1.0×10$^9$ M$^{-1}$ for L-selectin, with no significant difference from that of mouse DREG-55 (FIG. 9).

Inhibition of adhesion of human PBMC binding to lymph node high endothelial venules by humanized DREG-55 and DREG-200

Figure 10:
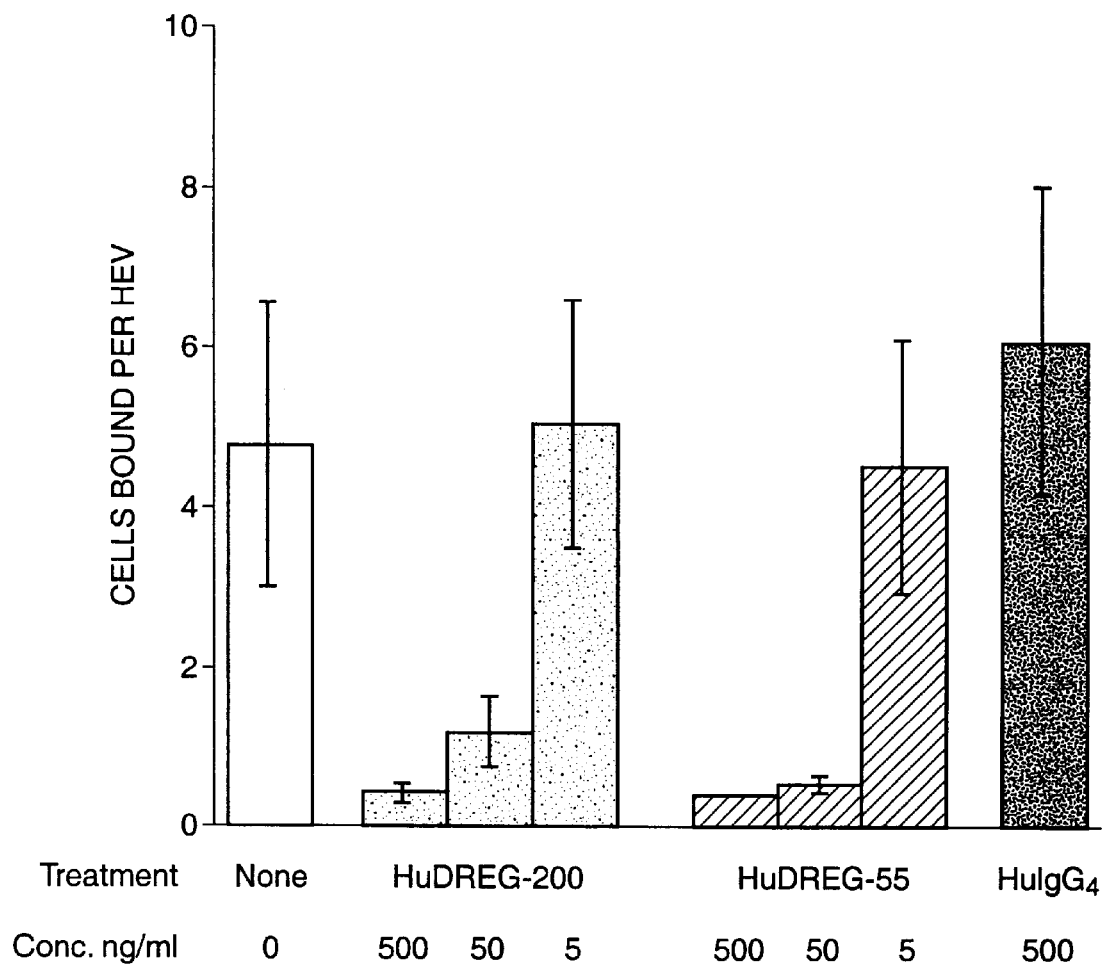
FIG. 10: Inhibition of binding of human PBMC to peripheral lymph node high endothelial venules by humanized DREG-55 (HuDREG-55) and humanized DREG-200 (HuDREG-200). The average number of cells bound per HEV for each antibody treatment is shown. Error bars show the standard errors of the values calculated for three sections.

Human peripheral blood mononuclear cells were isolated and cultured for 2 days at 37° C. in 10% FBS/DMEM. After washing and resuspending in assay medium (5% FBS/DMEM/10 mM HEPES, pH 6.9) at 7×10$^6$/ml in the presence of the indicated concentrations of humanized DREG-55, humanized DREG-200 or negative control antibody, cells were applied to frozen sections of mouse peripheral lymph nodes (PLN) while rotating at 50 rpm (as described in Streeter et al., Cell 107, 1853 (1988)). After 25 minutes, non-adherent cells were gently dumped and adherent cells fixed to sections by immersion in 1.5% glutaraldehyde-PBS. Slides were counterstained with thionine and the number of cells bound to each high endothelial venule (HEV) (n=60) in triplicate sections was determined microscopically. The average number of cells bound per HEV for each treatment was calculated. Results showed that humanized DREG-55 and humanized DREG-200 block adhesion of human peripheral blood mononuclear cells (PBMC) to lymph node high endothelial venules while the control antibody does not (FIG. 10).

Animal cross-reactivity of humanized DREG-55 and DREG-200

Cross-reactivity of humanized DREG-55 and humanized DREG-200 with blood leukocytes from various animal species was determined by FACS analysis. The cross-reactivity of DREG-200 with rabbit leukocytes and humanized DREG-200 with cat leukocytes has been reported in the literature (Buerke et. al., J. Pharm. Exp. Therap. 271, 134 (1994) and von Andrian et. al., Proc. Natl. Acad. Sci. USA 88, 7538 (1991)). While L-selectin is rapidly shed from neutrophils after activation by various chemotactic stimuli (Kishimoto et al., Science 245, 1238 (1989)), lymphocytes are not so affected (Hamann et al., J. Immunol. 140, 737 (1988) and Griffin et al., J. Immunol. 145, 576 (1990)). Thus, in all cases, both neutrophils and lymphocytes were included in these analyses.

Antibodies were purified by Protein A affinity chromatography from the supernatants from hybridoma or SP2/0 transfectoma cell lines grown in serum-free or low-serum-containing medium. Control antibodies tested include mouse IgG1 myeloma protein MOPC 21, purified human IgG4 (Sigma, St. Louis Mo.), and humanized ABL 364 (IgG4) (a humanized IgG4 antibody reactive with Lewis Y antigen). Secondary antibodies employed were phycoerythrin-conjugated goat F(ab')$_2$ anti-mouse IgG and phycoerythrin-conjugated goat F(ab')$_2$ anti-human IgG (Tago, Burlingame Calif.).

Leukocytes were prepared by a 20 min centrifugation at 1000 g of 5–15 ml heparinized blood diluted to 10–30 ml in Hanks Balanced Salt Solution without calcium or magnesium (HBSS) and layered over a 5–10 ml cushion of Histopaque 1077 or 1119 (Sigma, St. Louis Mo.). In some cases, blood was stored overnight at 4° C. prior to analysis. Leukocytes were washed twice and resuspended to $5 \times 10^6$/ml in FACS Buffer (0.1% bovine serum albumin, phosphate buffered saline (PBS), pH 7.2, 5 mM sodium azide). 100 Al aliquots were incubated with primary antibody (10 $\mu$l of 50 $\mu$g/ml). After a 1 hr incubation at 4° C., cells were washed with 4 ml FACS Buffer. The appropriate secondary antibody was added (usually 40 $\mu$l of 1:400 dilution in FACS Buffer) and cells were further incubated for 45 minutes in the dark at 4° C. After washing in 4 ml FACS Buffer, cells were resuspended in 1% paraformaldehyde prepared in PBS. Alternatively, in cases where there was significant red blood cell contamination, cells were treated with FACS lysing buffer (Becton Dickinson Immunocytometry, San Jose Calif.) according to the manufacturer's recommended protocol. Cells were analyzed on a Becton Dickinson FACScan (San Jose Calif.) by standard methods. Neutrophils and lymphocytes were gated by their distinctive side and forward scatter profiles. Controls always included unstained samples, samples treated with secondary antibodies alone, and samples treated with isotype-matched control antibodies in addition to the appropriate secondary antibody. Results of FACS analysis of leukocytes prepared from the following animals are shown in Table 4:

TABLE 4

Summary of FACB staining analysis of leukocyte populations

| Species | Mouse DREG-55 | Mouse DREG-200 | Hu DREG-55 | Hu DREG-200 |
|---|---|---|---|---|
| mouse | – | – | – | – |
| hamster | – | – | – | – |
| rat | – | – | ND | ND |
| rabbit | – | ++ | – | ++ |
| guinea pig | – | – | ND | ND |
| dog | – | – | – | – |

TABLE 4-continued

Summary of FACB staining analysis of leukocyte populations

| Species | Mouse DREG-55 | Mouse DREG-200 | Hu DREG-55 | Hu DREG-200 |
|---|---|---|---|---|
| pig | – | – | ND | ND |
| sheep | – | – | ND | ND |
| goat | – | – | ND | ND |
| cynomologous monkey | ++ | – | ++ | – |
| rhesus macaque | ++ | – | ++ | – |
| baboon | ++ | – | ++ | – |
| chimpanzee | ++ | ++ | ++ | ++ |
| cotton topped tamarin | ++ | – | ++ | – |
| human | ++ | ++ | ++ | ++ |

A negative (–) indicates that the mean fluorescence intensity (MFI) was less than 2-fold above the MFI of a sample stained with an isotype matched control antibody. Positive reactivity (++) indicates that the MFI of the sample was at least 10-fold above the MFI of a sample stained with an isotype-matched control antibody.
ND, not done.

The capacity of humanized DREG-55 to bind to cynomologous monkey, rhesus macaque, baboon and cotton topped tamarin, which is not shared by humanized DREG-200, is of advantage in conducting in vivo trials.

From the foregoing, it will be appreciated that the immunoglobulins of the present invention offer numerous advantages over other L-selectin specific antibodies. In comparison to mouse monoclonal antibodies, the present immunoglobulins can be more economically produced and contain substantially less foreign amino acid sequences. This reduced likelihood of antigenicity after injection into a human patient represents a significant therapeutic improvement.

All publications and patent applications cited above are herein incorporated by reference in their entirety for all purposes to the same extent as if each individual publication or patent application were specifically and individually indicated to be so incorporated by reference. Although the present invention has been described in some detail by way of illustration and example for purposes of clarity and understanding, it will be apparent that certain changes and modifications may be practiced within the scope of the appended claims.

SEQUENCE LISTING (1) GENERAL INFORMATION:

(iii) NUMBER OF SEQUENCES: 20

(2) INFORMATION FOR SEQ ID NO:1:

(i) SEQUENCE CHARACTERISTICS:
      (A) LENGTH: 399 base pairs
      (B) TYPE: nucleic acid
      (C) STRANDEDNESS: single
      (D) TOPOLOGY: linear (ii) MOLECULE TYPE: cDNA (ix) FEATURE:
    (A) NAME/KEY: CDS
    (B) LOCATION: 1..399

(xi) SEQUENCE DESCRIPTION: SEQ ID NO:1:

```
ATG GAA TCA CAG ACC CAG GTC CTC ATG TTT CTT CTG CTC TGG GTA TCT      48
Met Glu Ser Gln Thr Gln Val Leu Met Phe Leu Leu Leu Trp Val Ser
 1               5                  10                  15

GGT GCC TGT GCA GAC ATT GTG ATG ACA CAG TCT CCA TCC TCC CTG GCT      96
Gly Ala Cys Ala Asp Ile Val Met Thr Gln Ser Pro Ser Ser Leu Ala
                20                  25                  30

ATG TCA GTA GGA CAG AAG GTC ACT ATG ACC TGC AAG TCC AGT CAG AGC     144
Met Ser Val Gly Gln Lys Val Thr Met Thr Cys Lys Ser Ser Gln Ser
        35                  40                  45

CTT TTA AAT AGT AGC AAT CAA AAG AAC TAT TTG GCC TGG TAC CAG CAG     192
Leu Leu Asn Ser Ser Asn Gln Lys Asn Tyr Leu Ala Trp Tyr Gln Gln
    50                  55                  60

AAA CCA GGA CAG TCT CCT AAA CTT CTG GTA TAC TTT GCA TCC ACT AGG     240
Lys Pro Gly Gln Ser Pro Lys Leu Leu Val Tyr Phe Ala Ser Thr Arg
65                  70                  75                  80

GAA TCT GGG GTC CCT GAT CGC TTC ATA GGC AGT GGA TCT GGG ACA GAT     288
Glu Ser Gly Val Pro Asp Arg Phe Ile Gly Ser Gly Ser Gly Thr Asp
                85                  90                  95

TTC ACT CTT ACC ATC AGC AGT GTG CAG GCT GAA GAC CTG GCA GAT TAC     336
Phe Thr Leu Thr Ile Ser Ser Val Gln Ala Glu Asp Leu Ala Asp Tyr
                100                 105                 110

TTC TGT CAC CAA CAT TAT AGC ACT CCG CTC ACG TTC GGT GCT GGG ACC     384
Phe Cys His Gln His Tyr Ser Thr Pro Leu Thr Phe Gly Ala Gly Thr
            115                 120                 125

AAG CTG GAG CTG AAA                                                  399
Lys Leu Glu Leu Lys
        130
```

(2) INFORMATION FOR SEQ ID NO:2:

(i) SEQUENCE CHARACTERISTICS:
       (A) LENGTH: 133 amino acids
       (B) TYPE: amino acid
       (D) TOPOLOGY: linear (ii) MOLECULE TYPE: protein (xi) SEQUENCE DESCRIPTION: SEQ ID NO:2:

```
Met Glu Ser Gln Thr Gln Val Leu Met Phe Leu Leu Leu Trp Val Ser
 1               5                  10                  15

Gly Ala Cys Ala Asp Ile Val Met Thr Gln Ser Pro Ser Ser Leu Ala
                20                  25                  30

Met Ser Val Gly Gln Lys Val Thr Met Thr Cys Lys Ser Ser Gln Ser
        35                  40                  45

Leu Leu Asn Ser Ser Asn Gln Lys Asn Tyr Leu Ala Trp Tyr Gln Gln
    50                  55                  60

Lys Pro Gly Gln Ser Pro Lys Leu Leu Val Tyr Phe Ala Ser Thr Arg
65                  70                  75                  80

Glu Ser Gly Val Pro Asp Arg Phe Ile Gly Ser Gly Ser Gly Thr Asp
                85                  90                  95

Phe Thr Leu Thr Ile Ser Ser Val Gln Ala Glu Asp Leu Ala Asp Tyr
                100                 105                 110

Phe Cys His Gln His Tyr Ser Thr Pro Leu Thr Phe Gly Ala Gly Thr
            115                 120                 125

Lys Leu Glu Leu Lys
```

(2) INFORMATION FOR SEQ ID NO:3:

(i) SEQUENCE CHARACTERISTICS:
        (A) LENGTH: 420 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..420

(xi) SEQUENCE DESCRIPTION: SEQ ID NO:3:

```
ATG GAA TGG AGT TGG ATA TTT CTC TTT CTC CTG TCA GGA ACT GCA GGT      48
Met Glu Trp Ser Trp Ile Phe Ile Phe Leu Leu Ser Gly Thr Ala Gly
 1               5                  10                  15

GTC CAC TCT GAG GTC CAG CTG CAG CAG TCT GGA CCT GAC CTG GTA AAG      96
Val His Ser Glu Val Gln Leu Gln Gln Ser Gly Pro Asp Leu Val Lys
             20                  25                  30

CCT GGG GCT TCA GTG AAG ATG TCC TGC AAG GCT TCT GGA TAC ACA TTC     144
Pro Gly Ala Ser Val Lys Met Ser Cys Lys Ala Ser Gly Tyr Thr Phe
         35                  40                  45

ACT AGC TAT GTT ATG CAC TGG GTG AAG CAG AAG CCT GGG CAG GGC CTT     192
Thr Ser Tyr Val Met His Trp Val Lys Gln Lys Pro Gly Gln Gly Leu
     50                  55                  60

GAG TGG ATT GGA TAT ATT TAT CCT TAC AAT GAT GGT ACT AAG TAC AAT     240
Glu Trp Ile Gly Tyr Ile Tyr Pro Tyr Asn Asp Gly Thr Lys Tyr Asn
 65                  70                  75                  80

GAG AAG TTC AAA GGC AAG GCC ACA CTG ACT TCA GAC AAA TCC TCC AGC     288
Glu Lys Phe Lys Gly Lys Ala Thr Leu Thr Ser Asp Lys Ser Ser Ser
                 85                  90                  95

ACA GCC TAC ATG GAG CTC AGC AGC TTG ACC TCT GAG GAC TCT GCG GTC     336
Thr Ala Tyr Met Glu Leu Ser Ser Leu Thr Ser Glu Asp Ser Ala Val
            100                 105                 110

TAT TAC TGT GCA AGG GAG GAG TAT GGT AAC TAC GTT CGG TAC TTC GAT     384
Tyr Tyr Cys Ala Arg Glu Glu Tyr Gly Asn Tyr Val Arg Tyr Phe Asp
        115                 120                 125

GTC TGG GGC GCA GGG ACC ACG GTC ACC GTC TCC TCA                     420
Val Trp Gly Ala Gly Thr Thr Val Thr Val Ser Ser
    130                 135                 140
```

(2) INFORMATION FOR SEQ ID NO:4:

(i) SEQUENCE CHARACTERISTICS:
        (A) LENGTH: 140 amino acids
        (B) TYPE: amino acid
        (D) TOPOLOGY: linear (ii) MOLECULE TYPE: protein (xi) SEQUENCE DESCRIPTION: SEQ ID NO:4:

```
Met Glu Trp Ser Trp Ile Phe Ile Phe Leu Leu Ser Gly Thr Ala Gly
 1               5                  10                  15

Val His Ser Glu Val Gln Leu Gln Gln Ser Gly Pro Asp Leu Val Lys
             20                  25                  30

Pro Gly Ala Ser Val Lys Met Ser Cys Lys Ala Ser Gly Tyr Thr Phe
         35                  40                  45

Thr Ser Tyr Val Met His Trp Val Lys Gln Lys Pro Gly Gln Gly Leu
     50                  55                  60
```

```
Glu Trp Ile Gly Tyr Ile Tyr Pro Tyr Asn Asp Gly Thr Lys Tyr Asn
 65                  70                  75                  80

Glu Lys Phe Lys Gly Lys Ala Thr Leu Thr Ser Asp Lys Ser Ser Ser
                 85                  90                  95

Thr Ala Tyr Met Glu Leu Ser Ser Leu Thr Ser Glu Asp Ser Ala Val
            100                 105                 110

Tyr Tyr Cys Ala Arg Glu Glu Tyr Gly Asn Tyr Val Arg Val Phe Asp
            115                 120                 125

Val Trp Gly Ala Gly Thr Thr Val Thr Val Ser Ser
130                 135                 140
```

(2) INFORMATION FOR SEQ ID NO:5:

(i) SEQUENCE CHARACTERISTICS:
        (A) LENGTH: 113 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:5:

```
Asp Ile Val Met Thr Gln Ser Pro Ser Leu Ala Met Ser Val Gly
1               5                  10                  15

Gln Lys Val Thr Met Thr Cys Lys Ser Ser Gln Ser Leu Leu Asn Ser
                20                  25                  30

Ser Asn Gln Lys Asn Tyr Leu Ala Trp Tyr Gln Gln Lys Pro Gly Gln
            35                  40                  45

Ser Pro Lys Leu Leu Val Tyr Phe Ala Ser Thr Arg Glu Ser Gly Val
 50                  55                  60

Pro Asp Arg Phe Ile Gly Ser Gly Ser Gly Thr Asp Phe Thr Leu Thr
 65                  70                  75                  80

Ile Ser Ser Val Gln Ala Glu Asp Leu Ala Asp Tyr Phe Cys His Gln
                 85                  90                  95

His Tyr Ser Thr Pro Leu Thr Phe Gly Ala Gly Thr Lys Val Glu Leu
             100                 105                 110

Lys
```

(2) INFORMATION FOR SEQ ID NO:6:

(i) SEQUENCE CHARACTERISTICS:
        (A) LENGTH: 113 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:6:

```
Asp Ile Gln Met Thr Gln Ser Pro Ser Thr Leu Ser Ala Ser Val Gly
1               5                  10                  15

Asp Arg Val Thr Ile Thr Cys Lys Ser Ser Gln Ser Leu Leu Asn Ser
                20                  25                  30

Ser Asn Gln Lys Asn Tyr Leu Ala Trp Tyr Gln Gln Lys Pro Gly Lys
            35                  40                  45

Ala Pro Lys Leu Leu Val Tyr Phe Ala Ser Thr Arg Glu Ser Gly Val
 50                  55                  60

Pro Asp Arg Phe Ile Gly Ser Gly Ser Gly Thr Asp Phe Thr Leu Thr
65                   70                  75                  80
```

```
Ile Ser Ser Leu Gln Pro Glu Asp Phe Ala Thr Tyr Phe Cys His Gln
                85                  90                  95

His Tyr Ser Thr Pro Leu Thr Phe Gly Gln Gly Thr Lys Val Glu Val
            100                 105                 110

Lys
```

(2) INFORMATION FOR SEQ ID NO:7:

(i) SEQUENCE CHARACTERISTICS:
        (A) LENGTH: 121 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

```
Glu Val Gln Leu Gln Gln Ser Gly Pro Asp Leu Val Lys Pro Gly Ala
1               5                   10                  15

Ser Val Lys Met Ser Cys Lys Ala Ser Gly Tyr Thr Phe Thr Ser Tyr
                20                  25                  30

Val Met His Trp Val Lys Gln Lys Pro Gly Gln Gly Leu Glu Trp Ile
            35                  40                  45

Gly Tyr Ile Tyr Pro Tyr Asn Asp Gly Thr Lys Tyr Asn Glu Lys Phe
        50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Glu Glu Tyr Gly Asn Tyr Val Arg Tyr Phe Asp Val Trp Gly
                100                 105                 110

Ala Gly Thr Thr Val Thr Val Ser Ser
            115                 120
```

(2) INFORMATION FOR SEQ ID NO:8:

(i) SEQUENCE CHARACTERISTICS:
        (A) LENGTH: 121 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
                20                  25                  30

Val Met His Trp Val Arg Gln Ala Pro Gly Gln Gly Leu Glu Trp Ile
            35                  40                  45

Gly Tyr Ile Tyr Pro Tyr Asn Asp Gly Thr Lys Tyr Asn Glu Lys Phe
        50                  55                  60

Lys Gly Arg Val Thr Ile Thr Ser Asp Glu Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Glu Tyr Gly Asn Tyr Val Arg Tyr Phe Asp Val Trp Gly
                100                 105                 110
```

```
Gln Gly Thr Leu Val Thr Val Ser Ser
        115                 120
```

(2) INFORMATION FOR SEQ ID NO:9:

(i) SEQUENCE CHARACTERISTICS:
        (A) LENGTH: 430 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 12..410

(xi) SEQUENCE DESCRIPTION: SEQ ID NO:9:

```
TCTAGACCAC C ATG GTT TTC ACA CCT CAG ATA CTT GGA CTT ATG CTT TTT        50
             Met Val Phe Thr Pro Gln Ile Leu Gly Leu Met Leu Phe
              1               5                  10

TGG ATT TCA GCC TCC AGA GGT GAT ATT CAG ATG ACT CAG TCT CCA TCC         98
Trp Ile Ser Ala Ser Arg Gly Asp Ile Gln Met Thr Gln Ser Pro Ser
 15              20                  25

ACT CTG AGT GCA TCA GTA GGA GAT CGT GTC ACT ATT ACA TGT AAG AGC        146
Thr Leu Ser Ala Ser Val Gly Asp Arg Val Thr Ile Thr Cys Lys Ser
 30              35                  40                  45

AGC CAA AGC CTT TTA AAT AGT AGC AAT CAA AAG AAC TAT TTG GCC TGG        194
Ser Gln Ser Leu Leu Asn Ser Ser Asn Gln Lys Asn Tyr Leu Ala Trp
                 50                  55                  60

TAC CAG CAG AAA CCA GGA AAG GCA CCT AAG CTT CTG GTA TAC TTT GCA        242
Tyr Gln Gln Lys Pro Gly Lys Ala Pro Lys Leu Leu Val Tyr Phe Ala
             65                  70                  75

TCC ACT AGG GGA TCT GGA GTC CCT GAT CGC TTC ATA GGT AGT GGA TCT        290
Ser Thr Arg Gly Ser Gly Val Pro Asp Arg Phe Ile Gly Ser Gly Ser
             80                  85                  90

GGT ACA GAT TTC ACT CTT ACC ATC AGC AGT CTG CAG CCA GAA GAC TTT        338
Gly Thr Asp Phe Thr Leu Thr Ile Ser Ser Leu Gln Pro Glu Asp Phe
     95                 100                 105

GCA ACA TAC TTC TGT CAC CAA CAT TAT AGC ACT CCG CTC ACG TTC GGT        386
Ala Thr Tyr Phe Cys His Gln His Tyr Ser Thr Pro Leu Thr Phe Gly
110             115                 120                     125

CAA GGT ACT AAG GTA GAA GTC AAG CGTAAGTACA CTTTTCTAGA                  430
Gln Gly Thr Lys Val Glu Val Lys
                130
```

(2) INFORMATION FOR SEQ ID NO:10:

(i) SEQUENCE CHARACTERISTICS:
        (A) LENGTH: 133 amino acids
        (B) TYPE: amino acid
        (D) TOPOLOGY: linear (ii) MOLECULE TYPE: protein (xi) SEQUENCE DESCRIPTION: SEQ ID NO:10:

```
Met Val Phe Thr Pro Gln Ile Leu Gly Leu Met Leu Phe Trp Ile Ser
 1               5                  10                  15

Ala Ser Arg Gly Asp Ile Gln Met Thr Gln Ser Pro Thr Leu Ser
             20                  25                  30

Ala Ser Val Gly Asp Arg Val Thr Ile Thr Cys Lys Ser Ser Gln Ser
             35                  40                  45

Leu Leu Asn Ser Ser Asn Gln Lys Asn Tyr Leu Ala Trp Tyr Gln Gln
         50                  55                  60
```

```
Lys Pro Gly Lys Ala Pro Lys Leu Leu Val Tyr Phe Ala Ser Thr Arg
 65                  70                  75                  80

Glu Ser Gly Val Pro Asp Arg Phe Ile Gly Ser Gly Ser Gly Thr Asp
                 85                  90                  95

Phe Thr Leu Thr Ile Ser Ser Leu Gln Pro Glu Asp Phe Ala Thr Tyr
            100                 105                 110

Phe Cys His Gln His Tyr Ser Thr Pro Leu Thr Phe Gly Gln Gly Thr
        115                 120                 125

Lys Val Glu Val Lys
    130
```

(2) INFORMATION FOR SEQ ID NO:11:

(i) SEQUENCE CHARACTERISTICS:
        (A) LENGTH: 451 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 12..431

(xi) SEQUENCE DESCRIPTION: SEQ ID NO:11:

```
TCTAGACCAC C ATG GGA TGG AGC TGT ATC ATC CTC TTC TTG GTA GCA ACA     50
             Met Gly Trp Ser Cys Ile Ile Leu Phe Leu Val Ala Thr
              1               5                  10

GCT ACA GGT GTC CAC TCC CAG GTC CAG CTG GTA CAG TCT GGA GCT GAA     98
Ala Thr Gly Val His Ser Gln Val Gln Leu Val Gln Ser Gly Ala Glu
         15                  20                  25

GTC AAG AAA CCT GGG AGC TCA GTG AAG GTA TCC TGC AAG GCT TCT GGA    146
Val Lys Lys Pro Gly Ser Ser Val Lys Val Ser Cys Lys Ala Ser Gly
 30                  35                  40                  45

TAC ACA TTC ACT AGC TAT GTT ATG CAC TGG GTG AGA CAG GCA CCT GGT    194
Tyr Thr Phe Thr Ser Tyr Val Met His Trp Val Arg Gln Ala Pro Gly
             50                  55                  60

CAA GGA CTC GAG TGG ATT GGA TAT ATT TAT CCT TAC AAT GAT GGT ACC    242
Gln Gly Leu Glu Trp Ile Gly Tyr Ile Tyr Pro Tyr Asn Asp Gly Thr
         65                  70                  75

AAG TAC AAT GAG AAG TTC AAA GGC CGA GTC ACA ATT ACT TCA GAC GAG    290
Lys Tyr Asn Glu Lys Phe Lys Gly Arg Val Thr Ile Thr Ser Asp Glu
 80                  85                  90

TCC ACT AAC ACA GCC TAC ATG GAA CTC AGC AGC TTG CGA TCG GAG GAC    338
Ser Thr Asn Thr Ala Tyr Met Glu Leu Ser Ser Leu Arg Ser Glu Asp
     95                 100                 105

ACT GCA GTC TAT TAC TGT GCA AGG GAG GAG TAT GGT AAC TAC GTT CGG    386
Thr Ala Val Tyr Tyr Cys Ala Arg Glu Glu Tyr Gly Asn Tyr Val Arg
110                 115                 120                 125

TAC TTC GAT GTC TGG GGC CAA GGT ACA CTG GTC ACA GTC TCC TCA        431
Tyr Phe Asp Val Trp Gly Gln Gly Thr Leu Val Thr Val Ser Ser
             130                 135                 140

GGTGAGTCCT AACTTCTAGA                                              451
```

(2) INFORMATION FOR SEQ ID NO:12:

(i) SEQUENCE CHARACTERISTICS:
        (A) LENGTH: 140 amino acids
        (B) TYPE: amino acid
        (D) TOPOLOGY: linear (ii) MOLECULE TYPE: protein (xi) SEQUENCE DESCRIPTION: SEQ ID NO:12:

```
Met Gly Trp Ser Cys Ile Ile Leu Phe Leu Val Ala Thr Ala Thr Gly
 1               5                  10                  15

Val His Ser Gln Val Gln Leu Val Gln Ser Gly Ala Glu Val Lys Lys
                20                  25                  30

Pro Gly Ser Ser Val Lys Val Ser Cys Lys Ala Ser Gly Tyr Thr Phe
            35                  40                  45

Thr Ser Tyr Val Met His Trp Val Arg Gln Ala Pro Gly Gln Gly Leu
        50                  55                  60

Glu Trp Ile Gly Tyr Ile Tyr Pro Tyr Asn Asp Gly Thr Lys Tyr Asn
 65                 70                  75                  80

Glu Lys Phe Lys Gly Arg Val Thr Ile Thr Ser Asp Glu Ser Thr Asn
                85                  90                  95

Thr Ala Tyr Met Glu Leu Ser Ser Leu Arg Ser Glu Asp Thr Ala Val
            100                 105                 110

Tyr Tyr Cys Ala Arg Glu Glu Tyr Gly Asn Tyr Val Arg Tyr Phe Asp
        115                 120                 125

Val Trp Gly Gln Gly Thr Leu Val Thr Val Ser Ser
130                 135                 140
```

(2) INFORMATION FOR SEQ ID NO:13:

(i) SEQUENCE CHARACTERISTICS:
        (A) LENGTH: 393 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..393

(xi) SEQUENCE DESCRIPTION: SEQ ID NO:13:

```
ATG GAG ACA GAC ACA ATC CTG CTA TGG GTG CTG CTG CTC TGG GTT CCA      48
Met Glu Thr Asp Thr Ile Leu Leu Trp Val Leu Leu Leu Trp Val Pro
 1               5                  10                  15

GGC TCC ACT GGT GAC ATT GTG TTG ACC CAA TCT CCA GCT TCT TTG TCT      96
Gly Ser Thr Gly Asp Ile Val Leu Thr Gln Ser Pro Ala Ser Leu Ser
                20                  25                  30

GTG TCT CTA GGG GAG AGG GCC TCC ATC TCC TGC AAG GCC AGC CAA AGT     144
Val Ser Leu Gly Glu Arg Ala Ser Ile Ser Cys Lys Ala Ser Gln Ser
            35                  40                  45

GTT GAT TAT GAT GGT GAT AGT TAT ATG AAC TGG TAC CAA CAG AAA CCA     192
Val Asp Tyr Asp Gly Asp Ser Tyr Met Asn Trp Tyr Gln Gln Lys Pro
        50                  55                  60

GGA CAG CCA CCC AAA CTC CTC ATC TAT GCT GCA TCC AAT CTA GAA TCT     240
Gly Gln Pro Pro Lys Leu Leu Ile Tyr Ala Ala Ser Asn Leu Glu Ser
 65                 70                  75                  80

GGG ATC CCA GCC AGG TTT AGT GGC AGT GGG TCT GGG ACA GAC TTC ACC     288
Gly Ile Pro Ala Arg Phe Ser Gly Ser Gly Ser Gly Thr Asp Phe Thr
                85                  90                  95

CTC AAC ATC CAT CCT GTG GAG GAG GAG GAT GCT GCA ACC TAT TAC TGT     336
Leu Asn Ile His Pro Val Glu Glu Glu Asp Ala Ala Thr Tyr Tyr Cys
            100                 105                 110

CAG CAA AGT AAT GAG GAT CCG TGG ACG TTC GGT GGA GGC ACC AAG CTG     384
Gln Gln Ser Asn Glu Asp Pro Trp Thr Phe Gly Gly Gly Thr Lys Leu
        115                 120                 125
```

```
GAA ATC AAA                                                           393
Glu Ile Lys
    130

(2) INFORMATION FOR SEQ ID NO:14:

(i) SEQUENCE CHARACTERISTICS:
        (A) LENGTH: 131 amino acids
        (B) TYPE: amino acid
        (D) TOPOLOGY: linear (ii) MOLECULE TYPE: protein (xi) SEQUENCE DESCRIPTION: SEQ ID NO:14:

Met Glu Thr Asp Thr Ile Leu Leu Trp Val Leu Leu Leu Trp Val Pro
 1               5                  10                  15

Gly Ser Thr Gly Asp Ile Val Leu Thr Gln Ser Pro Ala Ser Leu Ser
            20                  25                  30

Val Ser Leu Gly Glu Arg Ala Ser Ile Ser Cys Lys Ala Ser Gln Ser
        35                  40                  45

Val Asp Tyr Asp Gly Asp Ser Tyr Met Asn Trp Tyr Gln Gln Lys Pro
 50                  55                  60

Gly Gln Pro Pro Lys Leu Leu Ile Tyr Ala Ala Ser Asn Leu Glu Ser
 65                  70                  75                  80

Gly Ile Pro Ala Arg Phe Ser Gly Ser Gly Ser Gly Thr Asp Phe Thr
                85                  90                  95

Leu Asn Ile His Pro Val Glu Glu Glu Asp Ala Ala Thr Tyr Tyr Cys
                100                 105                 110

Gln Gln Ser Asn Glu Asp Pro Trp Thr Phe Gly Gly Thr Lys Leu
            115                 120                 125

Glu Ile Lys
    130

(2) INFORMATION FOR SEQ ID NO:15:

(i) SEQUENCE CHARACTERISTICS:
        (A) LENGTH: 405 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..405

(xi) SEQUENCE DESCRIPTION: SEQ ID NO:15:

ATG AAC TTC GGG TCC AGC TTG ATT TTC CTT GTC CTT GTT TTA AAA GGT     48
Met Asn Phe Gly Ser Ser Leu Ile Phe Leu Val Leu Val Leu Lys Gly
 1               5                  10                  15

GTC CAG TGT GAA GTG AAA CTG GTG GAG TCT GGG GGA GGC TTA GTG AAG     96
Val Gln Cys Glu Val Lys Leu Val Glu Ser Gly Gly Gly Leu Val Lys
            20                  25                  30

CCT GGA GGG TCC CTG AAA CTC GCC TGT GCC GCC TCT GGA TTC ACT TTC    144
Pro Gly Gly Ser Leu Lys Leu Ala Cys Ala Ala Ser Gly Phe Thr Phe
        35                  40                  45

AGT ACC TAT GCC ATG TCT TGG GTT CGC CAG ACT CCA GAG AAG AGG CTG    192
Ser Thr Tyr Ala Met Ser Trp Val Arg Gln Thr Pro Glu Lys Arg Leu
 50                  55                  60

GAG TGG GTC GCA TCC ATT AGT ACT GGT GGT AGC ACC TAC TAT CCA GAC    240
Glu Trp Val Ala Ser Ile Ser Thr Gly Gly Ser Thr Tyr Tyr Pro Asp
```

```
                65                      70                      75                      80
AGT GTG AAG GGC CGA TTC ACC ATC TCC AGA GAT AAT GCC AGG AAC ATC        288
Ser Val Lys Gly Arg Phe Thr Ile Ser Arg Asp Asn Ala Arg Asn Ile
                        85                      90                      95

CTG TAC CTG CAA ATG AGC AGT CTG AGG TCT GAG GAC ACG GCC ATG TAT        336
Leu Tyr Leu Gln Met Ser Ser Leu Arg Ser Glu Asp Thr Ala Met Tyr
                100                     105                     110

TAC TGT GCA AGA GAC TAT GAC GGG TAT TTT GAC TAC TGG GGG CAA GGC        384
Tyr Cys Ala Arg Asp Tyr Asp Gly Tyr Phe Asp Tyr Trp Gly Gln Gly
        115                     120                     125

ACC ACT CTC ACA GTC TCC TCA                                            405
Thr Thr Leu Thr Val Ser Ser
130                     135

(2) INFORMATION FOR SEQ ID NO:16:

(i) SEQUENCE CHARACTERISTICS:
        (A) LENGTH: 135 amino acids
        (B) TYPE: amino acid
        (D) TOPOLOGY: linear (ii) MOLECULE TYPE: protein (xi) SEQUENCE DESCRIPTION: SEQ ID NO:16:

Met Asn Phe Gly Ser Ser Leu Ile Phe Leu Val Leu Val Leu Lys Gly
 1               5                  10                  15

Val Gln Cys Glu Val Lys Leu Val Glu Ser Gly Gly Gly Leu Val Lys
            20                  25                  30

Pro Gly Gly Ser Leu Lys Leu Ala Cys Ala Ala Ser Gly Phe Thr Phe
        35                  40                  45

Ser Thr Tyr Ala Met Ser Trp Val Arg Gln Thr Pro Glu Lys Arg Leu
    50                  55                  60

Glu Trp Val Ala Ser Ile Ser Thr Gly Gly Ser Thr Tyr Tyr Pro Asp
65                  70                  75                  80

Ser Val Lys Gly Arg Phe Thr Ile Ser Arg Asp Asn Ala Arg Asn Ile
                85                  90                  95

Leu Tyr Leu Gln Met Ser Ser Leu Arg Ser Glu Asp Thr Ala Met Tyr
            100                 105                 110

Tyr Cys Ala Arg Asp Tyr Asp Gly Tyr Phe Asp Tyr Trp Gly Gln Gly
        115                 120                 125

Thr Thr Leu Thr Val Ser Ser
    130                 135

(2) INFORMATION FOR SEQ ID NO:17:

(i) SEQUENCE CHARACTERISTICS:
        (A) LENGTH: 393 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..393

(xi) SEQUENCE DESCRIPTION: SEQ ID NO:17:

ATG GAG ACA GAC ACA ATC CTG CTA TGG GTG CTG CTG CTC TGG GTT CCA         48
Met Glu Thr Asp Thr Ile Leu Leu Trp Val Leu Leu Leu Trp Val Pro
 1               5                  10                  15

GGC TCC ACT GGT GAC ATT CAG ATG ACC CAA TCT CCG AGC TCT TTG TCT         96
```

```
Gly Ser Thr Gly Asp Ile Gln Met Thr Gln Ser Pro Ser Ser Leu Ser
             20                  25                  30

GCG TCT GTA GGG GAT AGG GTC ACT ATC ACC TGC AAG GCC AGC CAA AGT         144
Ala Ser Val Gly Asp Arg Val Thr Ile Thr Cys Lys Ala Ser Gln Ser
         35                  40                  45

GTT GAT TAT GAT GGT GAT AGT TAT ATG AAC TGG TAC CAA CAG AAA CCA         192
Val Asp Tyr Asp Gly Asp Ser Tyr Met Asn Trp Tyr Gln Gln Lys Pro
     50                  55                  60

GGC AAG GCA CCC AAG CTT CTC ATC TAT GCT GCA TCC AAC CTA GAA TCT         240
Gly Lys Ala Pro Lys Leu Leu Ile Tyr Ala Ala Ser Asn Leu Glu Ser
 65                  70                  75                  80

GGT ATC CCA TCC AGG TTT AGT GGC AGT GGG TCT GGG ACA GAC TTC ACC         288
Gly Ile Pro Ser Arg Phe Ser Gly Ser Gly Ser Gly Thr Asp Phe Thr
                 85                  90                  95

CTC ACC ATC TCT TCT CTG CAG CCG GAG GAT TTC GCA ACC TAT TAC TGT         336
Leu Thr Ile Ser Ser Leu Gln Pro Glu Asp Phe Ala Thr Tyr Tyr Cys
             100                 105                 110

CAG CAA AGT AAT GAA GAT CCG TGG ACG TTC GGT CAA GGC ACC AAG GTG         384
Gln Gln Ser Asn Glu Asp Pro Trp Thr Phe Gly Gln Gly Thr Lys Val
         115                 120                 125

GAA ATC AAA                                                             393
Glu Ile Lys
    130

(2) INFORMATION FOR SEQ ID NO:18:

(i) SEQUENCE CHARACTERISTICS:
        (A) LENGTH: 131 amino acids
        (B) TYPE: amino acid
        (D) TOPOLOGY: linear (ii) MOLECULE TYPE: protein (xi) SEQUENCE DESCRIPTION: SEQ ID NO:18:

Met Glu Thr Asp Thr Ile Leu Leu Trp Val Leu Leu Leu Trp Val Pro
 1               5                  10                  15

Gly Ser Thr Gly Asp Ile Gln Met Thr Gln Ser Pro Ser Ser Leu Ser
             20                  25                  30

Ala Ser Val Gly Asp Arg Val Thr Ile Thr Cys Lys Ala Ser Gln Ser
         35                  40                  45

Val Asp Tyr Asp Gly Asp Ser Tyr Met Asn Trp Tyr Gln Gln Lys Pro
     50                  55                  60

Gly Lys Ala Pro Lys Leu Leu Ile Tyr Ala Ala Ser Asn Leu Glu Ser
 65                  70                  75                  80

Gly Ile Pro Ser Arg Phe Ser Gly Ser Gly Ser Gly Thr Asp Phe Thr
                 85                  90                  95

Leu Thr Ile Ser Ser Leu Gln Pro Glu Asp Phe Ala Thr Tyr Tyr Cys
             100                 105                 110

Gln Gln Ser Asn Glu Asp Pro Trp Thr Phe Gly Gln Gly Thr Lys Val
         115                 120                 125

Glu Ile Lys
    130

(2) INFORMATION FOR SEQ ID NO:19:

(i) SEQUENCE CHARACTERISTICS:
        (A) LENGTH: 405 base pairs
        (B) TYPE: nucleic acid
        (C) STRANDEDNESS: single
        (D) TOPOLOGY: linear
```

(ii) MOLECULE TYPE: cDNA (ix) FEATURE:
    (A) NAME/KEY: CDS
    (B) LOCATION: 1..405

(xi) SEQUENCE DESCRIPTION: SEQ ID NO:19:

```
ATG AAC TTC GGG TCC AGC TTG ATT TTC CTT GTC CTT GTT TTA AAA GGT      48
Met Asn Phe Gly Ser Ser Leu Ile Phe Leu Val Leu Val Leu Lys Gly
 1               5                  10                  15

GTC CAG TGT GAA GTG CAA CTG GTG GAG TCT GGG GGA GGC TTA GTG CAG      96
Val Gln Cys Glu Val Gln Leu Val Glu Ser Gly Gly Gly Leu Val Gln
                20                  25                  30

CCT GGA GGA AGC TTG AGA CTC TCC TGT GCA GCC TCT GGA TTC ACT TTC     144
Pro Gly Gly Ser Leu Arg Leu Ser Cys Ala Ala Ser Gly Phe Thr Phe
            35                  40                  45

AGT ACC TAT GCC ATG TCT TGG GTT CGC CAG GCT CCA GGG AAG GGA CTC     192
Ser Thr Tyr Ala Met Ser Trp Val Arg Gln Ala Pro Gly Lys Gly Leu
 50                  55                  60

GAG TGG GTC GCA TCC ATT AGT ACT GGT GGT AGC ACC TAC TAT CCA GAC     240
Glu Trp Val Ala Ser Ile Ser Thr Gly Gly Ser Thr Tyr Tyr Pro Asp
 65                  70                  75                  80

AGT GTG AAG GGC CGA TTC ACC ATC TCC AGA GAT AAT GCC AAG AAC ACC     288
Ser Val Lys Gly Arg Phe Thr Ile Ser Arg Asp Asn Ala Lys Asn Thr
                85                  90                  95

CTG TAC CTG CAA ATG AAT TCT CTG AGG GCT GAG GAC ACG GCC GTG TAT     336
Leu Tyr Leu Gln Met Asn Ser Leu Arg Ala Glu Asp Thr Ala Val Tyr
            100                 105                 110

TAC TGT GCA AGA GAC TAT GAC GGG TAT TTT GAC TAC TGG GGC CAA GGC     384
Tyr Cys Ala Arg Asp Tyr Asp Gly Tyr Phe Asp Tyr Trp Gly Gln Gly
        115                 120                 125

ACC CTG GTC ACA GTC TCC TCA                                         405
Thr Leu Val Thr Val Ser Ser
        130                 135
```

(2) INFORMATION FOR SEQ ID NO:20:

(i) SEQUENCE CHARACTERISTICS:
        (A) LENGTH: 135 amino acids
        (B) TYPE: amino acid
        (D) TOPOLOGY: linear (ii) MOLECULE TYPE: protein (xi) SEQUENCE DESCRIPTION: SEQ ID NO:20:

```
Met Asn Phe Gly Ser Ser Leu Ile Phe Leu Val Leu Val Leu Lys Gly
 1               5                  10                  15

Val Gln Cys Glu Val Gln Leu Val Glu Ser Gly Gly Gly Leu Val Gln
                20                  25                  30

Pro Gly Gly Ser Leu Arg Leu Ser Cys Ala Ala Ser Gly Phe Thr Phe
            35                  40                  45

Ser Thr Tyr Ala Met Ser Trp Val Arg Gln Ala Pro Gly Lys Gly Leu
 50                  55                  60

Glu Trp Val Ala Ser Ile Ser Thr Gly Gly Ser Thr Tyr Tyr Pro Asp
 65                  70                  75                  80

Ser Val Lys Gly Arg Phe Thr Ile Ser Arg Asp Asn Ala Lys Asn Thr
```

-continued

```
                      85                  90                      95
Leu Tyr Leu Gln Met Asn Ser Leu Arg Ala Glu Asp Thr Ala Val Tyr
            100                 105                 110
Tyr Cys Ala Arg Asp Tyr Asp Gly Tyr Phe Asp Tyr Trp Gly Gln Gly
            115                 120                 125
Thr Leu Val Thr Val Ser Ser
    130                 135
```

What is claimed is:

1. A humanized immunoglobulin having complementarity determining regions (CDRs) corresponding to CDRs from the mouse DREG-55 donor immunoglobulin and heavy and light chain variable region frameworks corresponding to human acceptor immunoglobulin heavy and light chain frameworks from the Gal antibody, provided that at least one position selected from the group consisting of L50, L62 and L74 is occupied by the amino acid present in the equivalent position of the mouse DREG-55 immunoglobulin light chain variable region framework, which humanized immunoglobulin specifically binds to human L-selectin with an affinity constant between $10^7$ $M^{-1}$ and five-fold the affinity of the mouse DREG-55 antibody, wherein the mouse DREG-55 antibody has light and heavy chain variable regions designated SEQ. ID. Nos. 14 and 16 respectively.

2. A humanized immunoglobulin according to claim 1 which is an antibody comprising two light chain/heavy chain dimers.

3. A humanized immunoglobulin of claim 2, wherein said antibody is of the IgG1 or IgG4 isotype.

4. A humanized immunoglobulin according to claim 1, wherein the humanized light chain comprises the mature light chain variable region of SEQ. ID. No. 18, and the humanized heavy chain comprises the mature heavy chain variable region of SEQ. ID. No. 20 except that one or more variable region framework residues may be substituted as shown in Tables 2 or 3.

5. A humanized immunoglobulin according to claim 1, wherein three or fewer amino acids from the donor immunoglobulin framework replace corresponding amino acids in the acceptor immunoglobulin heavy or light chain frameworks.

6. A humanized immunoglobulin according to claim 1 that binds to L-selectin from cynomologous monkey, rhesus macaque, baboon and cotton topped tamarin.

7. A humanized immunoglobulin according to claim 1 that has a binding affinity to L-selectin of about $10^9$ $M^{-1}$.

8. A humanized immunoglobulin according to claim 1, which is purified to at least 95% homogeneity.

9. A humanized immunoglobulin according to claim 1 that inhibits the binding of human neutrophils to human endothelial cells.

10. A humanized immunoglobulin, wherein the amino acid sequence of the mature light chain variable region is shown in the lower lines of FIG. 2A (SEQ. ID. No. 6) and the amino acid sequence of the mature heavy chain variable region is shown in the lower lines of FIG. 2B (SEQ. ID. No. 8).

11. A humanized immunoglobulin, wherein the amino acid sequence of the mature light chain variable region is shown in the lower lines of FIG. 7A (SEQ. ID. No. 18) and the amino acid sequence of the mature heavy chain variable region is shown in the lower lines of FIG. 7B SEQ. ID, No. 20).

12. A mammalian cell line expressing the humanized immunoglobulin of claim 11, wherein the cell line can be propagated in a serum-free medium to produce the humanized immunoglobulin.

13. A humanized immunoglobulin having complementarity determining regions (CDRs) corresponding to CDRs from the mouse DREG-200 donor immunoglobulin and heavy and light chain variable region frameworks corresponding to a human acceptor immunoglobulin heavy and light chain frameworks from the Eu antibody, provided that at least one position selected from the group consisting of L87, L54, L66, L76 and at least one position selected from the group consisting of H93, H95, H98, H111, H112, H115, H30, H98, H111, H27, H30, H48 and H72, is occupied by the amino acid present in the equivalent position of the mouse DREG-200 immunoglobulin light or heavy chain variable region framework, which humanized immunoglobulin specifically binds to human L-selectin with an affinity constant between $10^7$ $M^{-1}$ and three-fold the affinity of the mouse DREG-200 antibody, wherein the mouse DREG-200 antibody has light and heavy chain variable regions designated SEQ. ID. Nos. 2 and 4 respectively.

14. A composition for treating inflammatory disease comprising a humanized immunoglobulin according to any one of claim 1 or 13 and a pharmaceutical carrier.

15. A method for prevention or treatment of reperfusion injury in a patient, the method comprising administering a pharmaceutical composition comprising a pharmaceutically acceptable carrier and an effective dose of a human or humanized monoclonal antibody as defined in claim 1 or 13 thereby inhibiting adherence of human leukocytes to human endothelial cells to prevent or treat the reperfusion injury.

16. A method according to claim 15, wherein the humanized immunoglobulin comprises the amino acid sequence of the mature light chain variable region as shown in the lower lines of FIG. 2A (SEQ. ID. No. 6] or FIG. 7A (SEQ. ID. No. 18) and the amino acid sequence of the mature heavy chain variable region as shown in the lower lines of FIG. 2B (SEQ. ID. No. 8) or respectively FIG. 7B (SEQ. ID. No. 20).

17. A method according to claim 15, wherein the reperfusion injury is du to myocardial infarction or balloon angioplasty.

* * * * *